US005958676A

United States Patent [19]
Olivo

[11] Patent Number: 5,958,676
[45] Date of Patent: *Sep. 28, 1999

[54] GENETICALLY ENGINEERED CELL LINES FOR DETECTING INFECTIOUS HERPESVIRUS AND METHODS THEREFOR

[75] Inventor: Paul D. Olivo, St. Louis, Mo.

[73] Assignee: Washington University, St. Louis, Mo.

[*] Notice: This patent is subject to a terminal disclaimer.

[21] Appl. No.: 08/846,026

[22] Filed: Apr. 25, 1997

Related U.S. Application Data

[63] Continuation-in-part of application No. 08/395,673, Feb. 28, 1995, Pat. No. 5,733,720, which is a continuation-in-part of application No. 07/900,279, Jun. 18, 1992, Pat. No. 5,418,132.

[51] Int. Cl.$^6$ .............................. C12Q 1/70; C12Q 1/66; C12Q 5/10; C07H 21/04
[52] U.S. Cl. ................................. 435/5; 435/8; 435/69.1; 435/69.7; 435/69.8; 435/70.1; 435/172.3; 435/207; 435/235.1; 435/320.1; 536/23.4; 536/23.72; 536/24.1
[58] Field of Search .................................. 435/5, 8, 69.1, 435/69.7, 69.8, 70.1, 172.3, 207, 235.1, 240.2, 320; 536/22.1, 23.4, 23.72, 24.1

[56] References Cited

U.S. PATENT DOCUMENTS

| | | |
|---|---|---|
| 5,070,012 | 12/1991 | Nolan et al. . |
| 5,273,876 | 12/1993 | Hock et al. ........................... 435/235.1 |
| 5,418,132 | 5/1995 | Olivo ........................................... 435/5 |

FOREIGN PATENT DOCUMENTS

| | | |
|---|---|---|
| 331356 | 9/1989 | European Pat. Off. . |
| 0 336 626 | 10/1989 | European Pat. Off. . |
| 363127 | 4/1990 | European Pat. Off. . |
| 441582 | 8/1991 | European Pat. Off. . |
| 2620030 | 3/1989 | France . |
| 2 197 653 | 5/1988 | United Kingdom . |
| WO 88/03167 | 10/1986 | WIPO . |
| WO 89/03878 | 5/1989 | WIPO . |
| WO 90/02797 | 3/1990 | WIPO . |
| WO 91/02797 | 3/1990 | WIPO . |
| WO 94/00468 | 1/1994 | WIPO . |

OTHER PUBLICATIONS

Stabell et al., Isolation of a cell line for rapid and sensitive histochemical assay for the detection of herpes simplex virus, *J. of Virological Methods*, 38:195–204 (1992).

Wymer et al., Immediate early and functional AP–1 cis–response elements are involved in the transcriptional regulation of the large subunit of herpes simplex virus type 2 ribonucleotide reductase (ICP10), *Virus Research*, 23:253–270 (1992).

Wymer et al., Papillomavirus trans–activator protein E2 activates expression from the promoter for the ribonucleotide reductase large subunit from herpes simplex virus type 2, *J. of General Viroloy*, 71:1817–1821 (1990).

Wymer et al., Identification of Immediate–Early–Type cis––Response Elements in the Promoter for the Ribonucleotide Reductase Large Subunit from Herpes Simplex Virus Type 2, *J. of Virology*, 63:2773–2784 (1989).

Ho et al., β–Galactosidase as a Marker in the Peripheral and Neural Tissues of the Herpes Simplex Virus–Infected Mouse, *Virology*, 167:279–283 (1988).

Janet D. Smith, Human Cytomegalovirus: Demonstration of Permissive Epithelial Cells and Nonpermissive Fibroblastic Cells in a Survey of Human Cell Lines, *J. of Virology*, 60:583–588 (1986).

Gleaves et al., Detection of Human Cytomegalovirus in Clinical Specimens by Centrifugation Culture with a Non-human Cell Line, *J. of Clinical Microbiology*, 30:1045–1048 (1992).

Geller et al., A Defective HSV–1 Vector Expresses *Escherichia coli* β–Galactosidase in Cultured Peripheral Neurons, *Science*, 241:1667–1669 (1988).

Mosca et al., Herpes simplex virus type–1 can reactivate transcription of latent human immunodeficiency virus, *Nature* 325:67–70 (1987).

Mosca et al., Activation of human immunodeficiency virus by herpesvirus infection: Identification of a region within the long terminal repeat that responds to a trans–acting factor encoded by herpes simplex virus 1, *Proc. Natl. Acad. Sci.*, 84:7408–7412 (1987).

Popik et al., Inhibition by interferon of herpes simplex virus type 1–activated transcription of tat–defective provirus, *Proc. Natl. Acad. Sci.*, 88:9573–9577 (1991).

Kimpton et al., Detection of Replication–Competent and Pseudotyped Human Immunodeficiency Virus with a Sensitive Cell Line on the Basis of Activation of an Integrated β–Galactosidase Gene, *J. of Virology*, 66:2232–2239 (1992).

Flanagan et al., A Bi–Functional Reporter Plasmid For The Simultaneous Transient Expression Assay of Two Herpes Simplex Virus Promoters, *Virus Genes*, 1:61–71 (1987).

(List continued on next page.)

*Primary Examiner*—Donna C. Wortman
*Assistant Examiner*—Jay Williams
*Attorney, Agent, or Firm*—Howell & Haferkamp, L.C.

[57] ABSTRACT

A diagnostic assay for detecting the presence of an infectious herpesvirus in a specimen and a genetically engineered cell line for use in such assay are disclosed. The cell line used in the assay expresses a reporter gene only if infectious herpesvirus is present in the specimen. The assay involves inoculating a DNA-transfected cell line with a specimen suspected of containing a herpesvirus, allowing a sufficient period of time for the herpesvirus infectious cycle to proceed, and detecting and quantifying the number of herpesvirus-infected cells to determine the number of infectious herpesvirus virions in the specimen. The cell line is a DNA-transfected cell line susceptible to infection by a herpesvirus which is stably transformed with a chimeric gene comprising a herpesvirus inducible promoter and a gene coding for an enzyme, the expression of the enzyme being dependent upon and quantitatively proportional to the presence of herpesvirus. A kit for such assay is also provided.

24 Claims, 29 Drawing Sheets

OTHER PUBLICATIONS

Weir et al., An insertion vector for the analysis of gene expression during herpes simplex virus infection, *Gene*, 89:271–274 (1990).

Bonerot et al., Towards a new method of detection of human retrovirus: activation of HIV–1 LacZ recombinant provirus by the tat gene product, *C. R. Acad. Sci. Paris*, 307:311–316 (1988).

Savatier et al., A novel system for screening antiretroviral agents, *J. of Virological Methods*, 26:229–236 (1989).

Watson et al., Separation and Characterization of Herpes Simplex Virus Type 1 Immediate–Early mRNA's, *J. of Virology*, 31:42–52 (1979).

Ikenaka et al., Reliable Transient Promoter Assay Using Fluorescein–di–β–D–galactopyranoside Substrate, *DNA and Cell Biology*, 9:279–286 (1990).

Rocancourt et al., Activation of a β–Galactosidase Recombinant Provirus: Application to Titration of Human Immunodeficiency Virus (HIV) and HIV–Infected Cells, *J. of Virology*, 64:2660–2668 (1990).

Ziegler et al., Herpes Simplex Virus Detection b Macroscopic Reading after Overnight Incubation and Immunoperoxidase Staining, *J. of Clinical Microbiology*, 26:2013–2017 (1988).

Puchhammer–Stockl et al., Establishment of PCR for the Early Diagnosis of Herpes Simplex Encephalitis, *J. of Medical Virology*, 32:77–82 (1990).

Roberts et al., Exploitation of a rapid and sensitive assay to analyze transactivation of the human immunodeficiency virus type 1 (HIV–1) long terminal repeat, *Antiviral Chemistry & Chemotherapy*, 1:139–148 (1990).

Goldstein et al., Herpes Simplex Virus Type 1–Induced Ribonucleotide Reductase Activity is Dispensable for Virus Growth and DNA Synthesis: Isolation and Characterization of an ICP6 lacZ Insertion Mutant, *J. of Virology*, 62:196–205 (1988).

Kowalski et al., Evaluation of Immunologic Tests for the Detection of Ocular Herpes Simplex Virus, *Opthal.*, 96:1583–1586 (1989).

Geller et al., Infection of cultured central nervous system neurons with a defective herpes simplex virus 1 vector results in stable expression of *Escherichia coli* β–galactosidase, *Proc. Natl. Acad. Sci.*, 871149–1153 (1990).

Chen et al., Mutational Analysis of the Sequence Encoding ICP0 from Herpes Simplex Virus Type 1, *Virology*, 180:207–220 (1991).

Alfred I. Geller, A system, using neural cell lines, to characterize HSV–1 vectors containing genes which affect neuronal physiology, or neuronal promoters, *J. of Neuroscience Methods*, 36:91–103 (1991).

Emerman et al., Quantitative Analysis of Gene Suppression in Integrated Retrovirus Vectors, *Molecular and Cellular Biology*, 6:792–800 (1986).

Kerr et al., Transcriptionally Defective Retroviruses Containing lacZ for the In Situ Detection of Endogenous Genes and Developmentally Regulated Chromatin, *Cold Spring Harbor Symp. Quant. Biol.*, 54:767–776 (1989).

Gleaves et al., Detection and Serotyping of Herpes Simplex Virus in MRC–5 Cells by Use of Centrifugation and Monoclonal Antibodies 16 h Postinoculation, *J. of Clinical Microbiology*, 21:29–32 (1985).

Joyner et al., Retrovirus long terminal repeats activate expression of coding sequences for the herpes simplex virus thymidine kinase gene, *Proc. Natl. Acad. Sci.*, 79:1573–1577 (1982).

Eisenberg et al., Promoter Domains Required for Expression of Plasmid–Borne Copies of the Herpes Simplex Virus Thymidine Kinase Gene in Virus–Infected Mouse Fibroblasts and Microinjected Frog Oocytes, *Molecular and Cellular Biology*, 5:1940–1947 (1985).

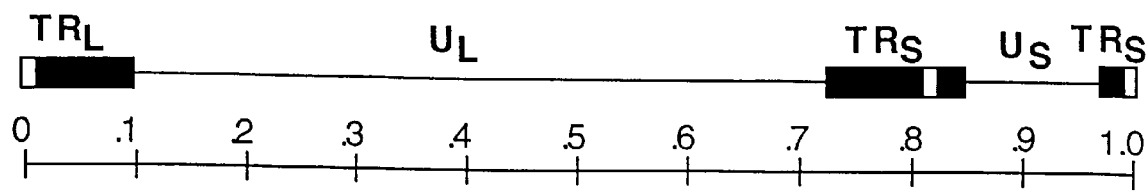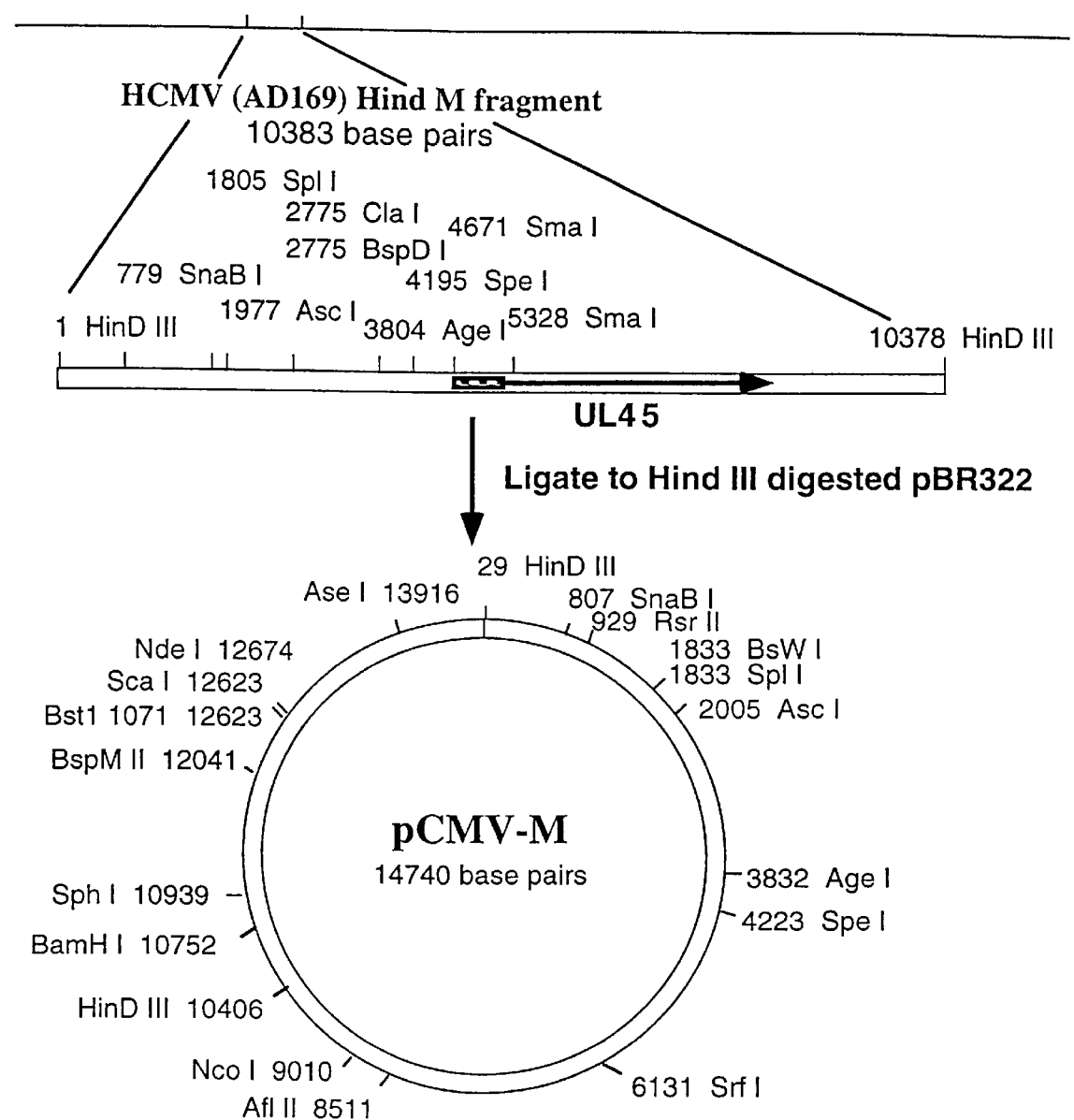
FIGURE 10

```
  1  cccggggacggctgcaatacgtgtatttaatcatcgtctatgactagtgacgggcccgaaacacgtcccgcatctacgtg    80

81  ctcacctccagcatcgcacactggcagacctggtcgacgttgcacgcggaaagttcgcccgcgagcgctgtagctttgt   160

161  caaccgtcgcatcacgcgccgccagatccctctgtgtacggggtcatacaaaagctgggctgtgtgcctggctgacg    240

241  acattcacacctcgttcctggtacacaagaactcaaactgtccgtcgtccgtttggacaactttagcgtcgaattggga   320

321  gactttcgagaattcgtctgagcggcgctgacagcatacggggaggagacacagaagaaaaacacatcgcacacagac    400

401  tttataaaccgtagttgtcggcgccatctagactcacttattgaaatctacctgattcttgttatttcctcgtaaa    480

481  ctt ATG AAT CCG GCT GAC GCG GAC GAG GAA CAG CGG GTG TCC TCG GTG CCC GCA CAT CGG  540
  1      M   N   P   A   D   A   D   E   E   Q   R   V   S   S   V   P   A   H   R   19

541  TGC CGG CCA GGT AGG ATT CCA AGC CGC AGC GCG GAA ACC GAG ACG GAG GAA TCG TCG GCA  600
 20   C   R   P   G   R   I   P   S   R   S   A   E   T   E   T   E   E   S   S   A   39

601  GAG GTC GCC GCT GAT ACT ATC GGG GGA GAT GAC AGC GAG CTC GAG GAG GGG CCG CTG CCC  660
 40   E   V   A   A   D   T   I   G   G   D   D   S   E   L   E   E   G   P   L   P   59

661  GGG                                                                             663
 60   G                                                                              60
```

FIGURE 11B

```
  1 cccggggacggctgcaatacgtgtatttaatcatcgtctatgactagtgacggcccgaaacacgtcccgcatctacgtg   80

81 ctcacctccagcatcgcacactggcagacccttggtcgacgttgcacgcggaaagttcgcccgcgagcgctagctttgt  160

161 caaccgtcgcatcacgcgccgcccagatccctctgtgtaccggtcatacaaagctgggctggtgcctggctgacg     240

241 acattcacacctcgttcctggtacacaaagaactcaaactgtccgtcgtcgtttgacaactttagcgtcgaattggga  320

321 gactttcgagaattcgtctgagcggctgacagcatacggggaggagacacagaagaaaaacatcgcacacagac      400

401 tttataaaccgtagttgtcggcgccatctagactcacttattgaaatctacctgatttctttgttatttcctcgtaaa   480

481 ctt ATG AAT CCG GCT GAC GCG GAC GAG GAA CAG CGG GTG TCC TCG CCC GCA CAT CGG  540
  1   M   N   P   A   D   A   D   E   E   Q   R   V   S   S   P   A   H   R     19

541 TGC CGG CCA GGT AGG ATT CCA AGC CGC GAA ACC GAG ACG GAG GAA TCG TCG GCA        600
 20   C   R   P   G   R   I   P   S   R   E   T   E   T   E   E   S   S   A      39

601 GAG GTC GCC GCT GAT ACT ATC GGG GGA GAT GAC AGC GAG GAG CTC GAG GGG CCG CTG CCC  660
 40   E   V   A   A   D   T   I   G   G   D   D   S   E   E   L   E   G   P   L   P  59

661 GGG GCC GTC GTT TTA CAA CGT CGT GAC TGG GAA AAC CCT GGC GTT ACC CAA CTT AAT CGC  720
 60   G   A   V   V   L   Q   R   R   D   W   E   N   P   G   V   T   Q   L   N   R  79

721 CTT GCA GCA CAT CCC CCT TTC GCC AGC CTG AAT GGC TGG CGT AAT AGC GAA GAG GCC ACC GAT CGC  780
 80   L   A   A   H   P   P   F   A   S   L   N   G   W   R   N   S   E   E   A   T   D   R  99

781 CCT TCC CAA CAG TTG CGC AGC CTG AAT GGC GAA TGG CGC TTT GCC TGG TTT CCG GCA CCA  840
100   P   S   Q   Q   L   R   S   L   N   G   E   W   R   F   A   W   F   P   A   P  119

841 GAA GCG GTG CCG GAA AGC TGG CTG GAG TGC GAT CTT CCT GAG GCC GAT ACT GTC GTC GTC  900
120   E   A   V   P   E   S   W   L   E   C   D   L   P   E   A   D   T   V   V   V  139

901 CCC TCA AAC TGG CAG ATG CAC GGT TAC GAT GCG CCC ATC TAC ACC AAC GTA ACC TAT CCC  960
140   P   S   N   W   Q   M   H   G   Y   D   A   P   I   Y   T   N   V   T   Y   P  159
```

FIGURE 13
(SHEET 1)

```
 961 ATT ACG GTC AAT CCG TTT GTT CCC ACG GAG AAT CCG ACG GGT TGT TAC TCG CTC ACA 1020
 160   I   T   V   N   P   F   V   P   T   E   N   P   T   G   C   Y   S   L   T   179

1021 TTT AAT GTT GAT GAA AGC TGG CTA CAG GAA GGC CAG ACG CGA ATT ATT TTT GAT GGC GTT 1080
 180   F   N   V   D   E   S   W   L   Q   E   G   Q   T   R   I   I   F   D   G   V   199

1081 AAC TCG GCG TTT CAT CTG TGG TGC AAC GCA TAC GGT GTC TGG CCG CAG GAC AGT CGT 1140
 200   N   S   A   F   H   L   W   C   N   A   Y   G   V   W   P   Q   D   S   R   219

1141 TTG CCG TCT GAA TTT GAC CTG AGC GCA GGA GAA AAC CGC CTC CAG GAC CTG GCG GTG 1200
 220   L   P   S   E   F   D   L   S   A   G   E   N   R   L   Q   D   L   A   V   239

1201 ATG GTG CTG CGT TGG AGT GAC GGC ATG TAC CTG CAG GAT CAG GAT ATG CGG ATG AGC 1260
 240   M   V   L   R   W   S   D   G   Y   L   Q   D   Q   D   M   R   M   S   259

1261 GGC ATT TTC TCG TTG CTG CAT AGC TAT CTG AAA CCG ACT CAA ATC GAA GAT TTC CAT 1320
 260   G   I   F   S   L   L   H   S   Y   L   K   P   T   Q   I   E   D   F   H   279

1321 GTT GCC ACT CGC TTT AAT GAT TTC AGC CGC GCT GTA CTG GAG CTG GCT CAG ATG 1380
 280   V   A   T   R   F   N   D   F   S   R   A   V   L   E   L   A   Q   M   299

1381 TGC GGC GAG TTG CGT ACA CGG TAC CTA CGG ACA GTT TCT TTA TGG ATC GAT GAG ACG 1440
 300   C   G   E   L   R   T   R   Y   L   R   T   V   S   L   W   I   D   E   T   319

1441 GTC GCC AGC GGC ACC GCG CCT TTC GGC AAC GTC GAA ATT AAA CTG TGG AGC TAT GCC 1500
 320   V   A   S   G   T   A   P   F   G   N   V   E   I   K   L   W   S   Y   A   339

1501 GAT CGC GTC ACA CTA CGT GGC GTG GTT GAA CTG CAC ACC GCC GAC GGC ACG CTG CCG 1560
 340   D   R   V   T   L   R   G   V   V   E   L   H   T   A   D   G   T   L   P   359

1561 AAT CTC TAT CGT TAT CGC TTC GAG GTT GTC GAG ATT GAA GCA GAA CTG CTG CAG GAA 1620
 360   N   L   Y   R   Y   R   F   E   V   V   E   I   E   A   E   L   L   Q   E   379

1621 GCC TGC GAT GTC GGT TTC CGC GAG GTG CGG ATT GAA AAT GGT CTG CTG CTG CTG AAC GGC 1680
 380   A   C   D   V   G   F   R   E   V   R   I   E   N   G   L   L   L   L   N   G   399
```

FIGURE 13
(SHEET 2)

```
1681 AAG CCG TTG CTG ATT CGA GGC GTT AAC CGT CAT CAT CCT CTG CAT GGT CAG GTC 1740
 400  K   P   L   L   I   R   G   V   N   R   H   H   P   L   H   G   Q   V   419

1741 ATG GAT GAG CAG ACG ATG GTG CAG GAT ATC CTG CTG AAG CAT AAC AAC TTT AAC GCC 1800
 420  M   D   E   Q   T   M   V   Q   D   I   L   L   K   H   N   N   F   N   A   439

1801 GTG CGC TGT TCG CAT TAT CCG AAC CAT CCG CTG TAC TAC ACG CTG TGC GAC CGC TAC GGC 1860
 440  V   R   C   S   H   Y   P   N   H   P   L   Y   Y   T   L   C   D   R   Y   G   459

1861 CTG TAT GTG GTG GAT GAA GCC AAT ATT GAA ACC CAT GGC ATG GTG CCA ATG AAT CGT CTG 1920
 460  L   Y   V   V   D   E   A   N   I   E   T   H   G   M   V   P   M   N   R   L   479

1921 ACC GAT GAT CCG CGC TGG CTA CCG CGC ATG AGC GAA CGC GTA ACG CGA ATG GTG CAG CGC 1980
 480  T   D   D   P   R   W   L   P   R   M   S   E   R   V   T   R   M   V   Q   R   499

1981 GAT CGT AAT CAC CCG AGT GTG ATC ATC TGG TCG CTG GGG AAT GAA TCA GGC CAC GGC GCT 2040
 500  D   R   N   H   P   S   V   I   I   W   S   L   G   N   E   S   G   H   G   A   519

2041 AAT CAC GAC GCG CTG TAT CGC TGG ATC AAA TCT GTC GAT CCT TCC CGC CCG GTG CAG TAT 2100
 520  N   H   D   A   L   Y   R   W   I   K   S   V   D   P   S   R   P   V   Q   Y   539

2101 GAA GGC GGA GGC GCC GAC ACC ACG GCT ACC GAT ATT ATT TGC CCA ATG TAC GCG CGC GTG 2160
 540  E   G   G   G   A   D   T   T   A   T   D   I   I   C   P   M   Y   A   R   V   559

2161 GAT GAA GAC CAG CCC TTC CCG GCT GTG CCG AAA TGG TCC ATC AAA AAA TGG CTT TCG CTA 2220
 560  D   E   D   Q   P   F   P   A   V   P   K   W   S   I   K   K   W   L   S   L   579

2221 CCT GGA GAG ACG CGC CCG CTG ATC CTT TGC GAA TAC GCC CAC GCC ATG GGT AAC AGT CTT 2280
 580  P   G   E   T   R   P   L   I   L   C   E   Y   A   H   A   M   G   N   S   L   599

2281 GGC GGT TTC GCT AAA TAC TGG CAG GCG TTT CGT CAG TAT CCC CGT TTA CAG GGC GGC TTC 2340
 600  G   G   F   A   K   Y   W   Q   A   F   R   Q   Y   P   R   L   Q   G   G   F   619

2341 GTC TGG GAC TGG GTG GAT CAG TCG CTG ATT AAA TAT GAT GAA AAC GGC AAC CCG TGG TCG 2400
 620  V   W   D   W   V   D   Q   S   L   I   K   Y   D   E   N   G   N   P   W   S   639
```

FIGURE 13 (SHEET 3)

```
2401 GCT TAC GGC GGT GAT TTT GGC GAT ACG CCG AAC GAT CGC CAG TTC TGT ATG AAC GGT CTG 2460
 640  A   Y   G   G   D   F   G   D   T   P   N   D   R   Q   F   C   M   N   G   L  659

2461 GTC TTT GCC GAC CGC ACG CCG CAT CCA GCG CTG ACG GAA GCA AAA CAC CAG CAG TTT 2520
 660  V   F   A   D   R   T   P   H   P   A   L   T   E   A   K   H   Q   Q   F  679

2521 TTC CAG TTC CGT TTA TCC GGG CAA ACC ATC GAA GTG TAC CTG GAA TAC CGT CAT 2580
 680  F   Q   F   R   L   S   G   Q   T   I   E   V   Y   L   F   R   H  699

2581 AGC GAT AAC GAG CTC CTG CAC TGG ATG GTG GCG CTG GAT GGT AAG CCG CTG GCA AGC GGT 2640
 700  S   D   N   E   L   L   H   W   M   V   A   L   D   G   K   P   L   A   S   G  719

2641 GAA GTG CCT CTG GAT GTC GCT CCA CAA GGT TTG ATT GAA CAG CTG CAA CCT GAA CTA CCG 2700
 720  E   V   P   L   D   V   A   P   Q   G   L   I   E   Q   L   Q   P   E   L   P  739

2701 CAG CCG GAG AGC GGG GCC CAA CTC ACA CAG GTA CGC CAG GTG GTA CCG CAA CCG AAC ACC 2760
 740  Q   P   E   S   G   A   Q   L   T   Q   V   R   Q   V   V   P   Q   P   N   T  759

2761 GCA TGG TCA GAA GCC GGG GGC ATC AGC CTC TGG CAG ATC CCG CAT CTG AAC CCG GCC GCG 2820
 760  A   W   S   E   A   G   G   I   S   L   W   Q   I   P   H   L   N   P   A   A  779

2821 AGT GTG ACG CTC ACC CCC GCC TCC CAC GCC ATC ACC AGC CAT CTG CGC CCG CTG GAA AAC 2880
 780  S   V   T   L   T   P   A   S   H   A   I   T   S   H   L   R   P   L   E   N  799

2881 TTT TGC ATC GAG CTG GGT GGT AAT AAG CGT CAA TTT CTG CAG TCA GGC TTT CTT 2940
 800  F   C   I   E   L   G   G   N   K   R   Q   F   L   Q   S   G   F   L  819

2941 CAG ATG TGG ATT GGC GAT AAA AAA CAA CTG ACG CGC CGC GAT CAG TTC ACC CGT 3000
 820  Q   M   W   I   G   D   K   K   Q   L   T   R   R   D   Q   F   T   R  839

3001 GCA CCG CTG GAT AAC GAC ATT GGC GTA AGT GAA GCG ACC ATT GAC CCT AAC GCC TGG 3060
 840  A   P   L   D   N   D   I   G   V   S   E   A   T   I   D   P   N   A   W  859

3061 GTC GAA CGC TGG AAG GCG GCG CAT TAC CAG GCC GAA GCA TTG TTG CAG TGC ACG 3120
 860  V   E   R   W   K   A   A   H   Y   Q   A   E   A   L   L   Q   C   T  879
```

FIGURE 13
(SHEET 4)

FIGURE 13 (SHEET 5)

```
3121 GCA GAT ACA CTT GCT GAT GCG GTG CTG ATT ACG ACC GCT CAC GCG TGG CAG CAT CAG GGG 3180
 880  A   D   T   L   A   D   A   V   L   I   T   T   A   H   A   W   Q   H   Q   G   899

3181 AAA ACC TTA TTT ATC AGC CGG AAA CGG CGG TAC CGG ATT GAT GGT CAA ATG CAA ATG GCG ATT 3240
 900  K   T   L   F   I   S   R   K   R   R   Y   R   I   D   G   Q   M   Q   M   A   I   919

3241 ACC GTT GAT GTT GAA GTG GCG AGC GAT ACA CCG CAT CCG GCG CGG ATT GGC AGT CTG AAC TGC 3300
 920  T   V   D   V   E   V   A   S   D   T   P   H   P   A   R   I   G   S   L   N   C   939

3301 CAG CTG GCG CAG GTA GCA GAG CGG GTA AAC TGG CTC GGA TTA GGG CCG CAA GAA AAC TAT 3360
 940  Q   L   A   Q   V   A   E   R   V   N   W   L   G   L   G   P   Q   E   N   Y   959

3361 CCC GAC CGC CTT ACT GCC GCC TGT TTT GAC CGC TGG GAT CTG CCA TTG TCA GAA ATG TAT 3420
 960  P   D   R   L   T   A   A   C   F   D   R   W   D   L   P   L   S   E   M   Y   979

3421 ACC CCG TAC GTC TTC CCG AGC GCC CGC AAC GGT CAG TTC CAG TGC CGC ACG CGC TAC AGT CAA GAA TTG AAT TAT 3480
 980  T   P   Y   V   F   P   S   A   R   N   G   Q   F   Q   C   R   T   R   Y   S   E   L   N   Y   999

3481 GGC CCA CAC CAG TGG CGC CGC AGC CAT CGC CAT CTG CTG CAC GAC GAC TCC TGG AGC ACA TGG CTG AAT ATC 3540
1000  G   P   H   Q   W   R   R   S   H   R   H   L   L   H   D   D   S   W   S   T   W   L   N   I   1019

3541 CTG ATG GAA ACC TTC CAT ATG GGG ATT GGT GGC GAC TAC CAG CGC TAC CAT TAC CAG TTG GTC TGG TGT CAA CAG ATC 3600
1020  L   M   E   T   F   H   M   G   I   G   G   D   Y   Q   R   Y   H   Y   Q   L   V   W   C   Q   Q   I   1039

3601 GAC GGT TTC CAT ATG GAA ACC AGC CAT CGC CGG ATT GGT GGC GAC TAC CAT TAC CGC TAC CAT TAC CAG TTG GTC TGG TGT CAA CAG ATC 3660
1040  D   G   F   H   M   E   T   S   H   R   R   I   G   G   D   Y   H   Y   R   Y   H   Y   Q   L   V   W   C   Q   Q   I   1059

3661 TTC CAG CTG AGC GAC GGT TTC CAT ATG GAA ACC AGC CAT CGC CGG ATT GGT GGC GAC TAC CAT TAC CGC TAC CGT TCA GTA TCG GCG GAA 3720
1060  F   Q   L   S   A   G   R   Y   H   Y   Q   L   V   W   C   Q   Q   I   F   Q   L   S   V   C   Q   K   *   1077

3723 atcctctagagtcgacctgcaggcatgcaagctt 3756
```

Beta Genes of Human Herpesviruses

| HSV-1 | HSV-2 | VZV | EBV | HCMV | HHV6 | HHV7 | HHV8 |
|---|---|---|---|---|---|---|---|
| UL2 | UL2 | gene 59 | BKRF3 | UL114 | U81 | U81 | ? |
| UL5 | UL5 | gene 55 | BBLF4 | UL105 | U77 | U77 | ? |
| UL8 | UL8 | gene 52 | BBLF3 | UL102 | U74 | U74 | ? |
| UL9 | UL9 | gene 51 | (nh) | (nh) | U73 | U73 | ? |
| UL12 | UL12 | gene 48 | BGLF5 | UL98 | U70 | U70 | ORF21 |
| UL23 | UL23 | gene 36 | BXLF1 | (nh) | (nh) | (nh) | ? |
| UL29 | UL29 | gene 29 | BALF2 | UL57 | U41 | U41 | ? |
| UL30 | UL30 | gene 28 | BALF5 | UL54 | U38 | U38 | ? |
| UL39 | UL39 | gene 19 | BORF2 | UL45 | U28 | U28 | ? |
| UL40 | UL40 | gene 18 | BaRF1 | (nh) | (nh) | (nh) | ? |
| UL42 | UL42 | gene 16 | BMRF1 | UL44 | U27 | U27 | ? |
| UL50 | UL50 | gene 8 | BLLF2 | UL72 | U45 | U45 | ? |
| UL52 | UL52 | gene 6 | BSLF1 | UL70 | U43 | U43 | ? |
| US3 | US3 | gene 66 | (nh) | (nh) | (nh) | (nh) | ? |
| (nh) | (nh) | (nh) | (nh) | UL101 | U55 | U55A/B | ? |
| (nh) | (nh) | (nh) | (nh) | UL84 | | | ? |
| (nh) | (nh) | (nh) | (nh) | UL112 | U79 | U79 | ? |

?: sequence information incomplete
(nh): no homolog

FIGURE 20

GENETICALLY ENGINEERED CELL LINES FOR DETECTING INFECTIOUS HERPESVIRUS AND METHODS THEREFOR

RELATED APPLICATIONS

This application is a continuation-in-part of the U.S. application, Ser. No. 08/395,673, filed Feb. 28, 1995, now U.S. Pat. No. 5,733,720 which in turn is a continuation-in-part of U.S. application, Ser. No. 07/900,279, filed Jun. 18, 1992, now U.S. Pat. No. 5,418,132, both of which are incorporated herein by reference.

BACKGROUND OF THE INVENTION

(1) Field of the Invention

This invention generally relates to the field of diagnostic virology and, more particularly, to a method for detecting infectious herpesvirus in a specimen and a cell line for use therefor.

(2) Description of the Related Art

Herpesviruses have been found in most animal species and approximately 100 herpesviruses have been at least partially characterized. These include species causing diseases in humans, horses, cattle, pigs, and chickens. In humans, the eight herpesviruses that have been thus far isolated are viewed as important causes of human morbidity and mortality. (Whitley, R. J., Virology (1990) New York, Raven Press which is incorporated by reference). Thus, the availability of methods for detecting infectious herpesviruses has become increasingly important.

The eight known human herpesviruses are herpes simplex virus type 1 (HSV-1), herpes simplex virus type 2 (HSV-2), human cytomegalovirus (HCMV), varicella-zoster virus (VZV), Epstein-Barr virus (EBV), human herpes virus 6 (HHV6), human herpes virus 7 (HHV7), and human herpes virus 8 (HHV8). The herpesviruses differ with respect to the diseases they cause. HSV-1 infection produces skin vesicles or mucosal ulcers generally limited to the oropharynx; HSV-2 produces mucocutaneous lesions generally in the genital region; HCMV can infect monocytes and a number of organ systems including salivary glands, kidneys, liver and lung; VZV causes the diseases of chickenpox and shingles; EBV infects the oropharyngeal epithelium and B lymphocytes; and HHV6 and HHV7 infect mononuclear cells and, in children, produce skin eruptions (Roseola Infantum). (Virology, Fields and Knipe, Eds., Raven Press, pp. 1795–2062, which is incorporated by reference).

All herpes virus have a linear double-stranded DNA genome and they all replicate in the nucleus of infected cells where viral gene expression during viral replication occurs as an ordered cascade. Genes expressed during viral replication are organized on the genome in a very straightforward manner; there are few overlapping genes, very few spliced genes, and the regulatory elements (for example, promoters) are immediately upstream of the open reading frames. All known herpes viruses have three major classes of herpesvirus genes, α, β, and γ, which have the same basic temporal pattern of expression during viral replication.

Alpha genes, also called immediate-early genes, are expressed very early after infection and the expression of each alpha gene does not require any other viral gene or gene product. The products of the alpha genes are predominantly involved in regulation of viral gene expression.

Beta (early) genes are expressed only after the alpha genes because their expression depends on the presence of one or more of the alpha gene products which act as transcriptional activators to upregulate the expression of the beta genes. Thus, one way that beta genes have been defined is by the observation that their expression from the viral genome is not reduced in infected cells when viral DNA synthesis is blocked, but there is a virtual absence of expression of their RNA transcripts when production of alpha gene products is prevented by blocking protein synthesis. The products of beta genes are primarily enzymes involved in viral nucleic acid synthesis and metabolism.

Gamma (late) genes are expressed either primarily ($\gamma 1$) or exclusively ($\gamma 2$) following viral DNA synthesis. Gamma gene products are primarily structural components of the virion.

Many studies have analyzed the regulation of herpesvirus gene expression using isolated herpesvirus genes or isolated herpesvirus promoters, outside the context of the viral genome. This experimental approach has contributed to the identification of the cis- and trans-acting factors involved in the regulation of the expression of many herpesvirus genes. Many studies have shown that isolated beta genes, such as the prototypical beta gene, the HSV thymidine kinase (tk) gene, when transfected into cells are capable of being upregulated by certain alpha genes (Eisenberg et al., Mol. Cell Biol. 5:1940–1947, 1985) which is incorporated herein by reference). The tk promoter has been shown to contain cis-acting elements that are found on many cellular promoters (Zipser et al., Proc. Natl. Acad. Sci USA 78:6276–6280, 1981, incorporated herein by reference). It is generally recognized that the promoter of beta genes is both necessary and sufficient for the transactivation of beta genes by alpha gene products.

The complete sequences of human herpesviruses HSV-1, HSV-2, HCMV, EBV, VZV, HHV6, HHV7 are known, and a partial sequence of HHV8 is known. (HSV-1, McGeoch et al., Nucleic Acids Res 14:1727–1745, 1986, McGeoch et al., J Gen Virol 69:1531–1574, 1988, GenBank Accession Nos.: X14112, D00317, D00374, and S40593); HSV-2, McGeoch et al., J. Gen. Virol. 72, 3057–3075, 1991, GenBank Accession No.: Z86099; HCMV, Chee et al., DNA Seq 2:1–12, 1991, GenBank Accession No.: X17403; EBV, Baer et al., Nature 310:207–211, 1984, GenBank Accession Nos.: V01555, J02070, K01729, K01730, V01554, X00498, X00499, and X00784; VSV, Davidson and Scott, J. Gen Virol 67:1759–1816, 1986, GenBank Accession Nos.: X04370, M14891, and M16612; HHV6, Gompels et al., Virology 209:29–51, 1995, GenBank Accession No.: X83413; HHV7, Nicholas, GenBank Accession No.: U43400; and HHV8, Russo et al., Proc. Natl. Acad. Sci. U.S.A. 93:14862–14867, 1996, GenBank Accession No.: U75698, each of which is incorporated by reference). Analysis of this sequence data has shown that the beta genes represent a limited number of genes in the genomes of all herpesviruses which have been studied and that beta genes are highly conserved in the herpesvirus family.

For example, in HSV-1 there are fourteen genes that have been classified as beta genes: UL2, UL5, UL8, UL9, UL12, UL23, UL29, UL30, UL39, UL40, UL42, UL50, UL52, and UL53 (Roizman et al., Herpes Simplex Viruses and Their Replication, Raven Press, Ltd. NY, pp. 1795–1841, 1990, incorporated herein by reference). These genes encode respectively, a uracil DNA glycosidase, a DNA helicase, a component of the DNA helicase/primase complex, an origin of DNA replication binding protein, a DNA exonuclease, a nucleoside kinase, a single-stranded DNA binding protein, a DNA polymerase, a ribonucleotide reductase large subunit, a ribonucleotide reductase small subunit, a double-stranded DNA binding protein which acts as a polymerase processivity factor, a dUTPase, a primase, and a protein kinase. All but one of these enzymes, the protein kinase, has been shown to be involved in DNA metabolism or to be directly involved in synthesis of viral DNA.

Based on standard DNA and predicted protein sequence alignment paradigms, it has been determined that HSV-2 and VZV have homologs for each of the fourteen HSV-1 beta genes (Davison et al., *J. Gen. Virol.* 67:1759–1816 1986, incorporated herein by reference). For example, the UL39 gene of HSV-1 encodes the large subunit of ribonucleotide reductase (RR), a two subunit enzyme involved in the generation of deoxyribnucleoside triphosphates, the immediate precursors of DNA. The ribonucleotide reductase large subunit of HSV-1, also known as RR1 or ICP6, has 38% homology at the N-terminal portion and 93% homology at the C-terminal portion of the corresponding HSV-2 protein, ICP10, which is encoded by the UL39 gene of HSV-2. (Nikas et al., *PROTEINS: Structure, Function, and Genetics* 1:376–384, 1986 which is incorporated by reference). In VZV, the corresponding ribonucleotide reductase large subunit is encoded by gene 19 and shows between 43% and 53% homology beginning at HSV-1 amino acid 384 and VZV amino acid 16. Id. Homologs to UL39, gene 19 and most of the other HSV and VZV beta genes have also been easily identified in more distantly related human herpesviruses such as Epstein-Barr virus (EBV) and human cytomegalovirus (HCMV) (Baer et al., *Nature* 310:207–211, 1984; Chee et al., *Curr. Top. Microbiol. immunol.* 154: 125–169, 1990, each of which is incorporated herein by reference). A listing of the homologous beta genes in the human herpesvirus family is shown in FIG. 20.

In those cases which have been studied, the products of these conserved genes have displayed remarkable conservation of function and all, except for the protein kinase gene, have been shown to have a role in viral DNA synthesis or metabolism. Moreover, in all cases studied, these genes exhibit a pattern of expression consistent with their being classified as beta genes.

Herpes simplex viruses Types 1 and 2 (hereinafter referred to collectively as HSV) infect a large number of individuals each year. Primary infection of immunocompetent patients with HSV usually leads to a mucocutaneous syndrome such as herpes labialis (HSV-1) or herpes genitalis (HSV-2), the latter being one of the most common sexually transmitted diseases today. Infection with HSV can also cause more serious infections, the most serious of which are sight-threatening keratitis and life-threatening encephalitis. Moreover, HSV related disease in immunocompromised individuals such as newborns, leukemia patients, organ transplant recipients and AIDS patients has become an increasingly prevalent and difficult problem.

Significant advances have been made in the treatment of herpesvirus infections in the past decade. These advances in antiviral therapy have expanded the role of the diagnostic virology laboratory and have identified the need for more sensitive, accurate and rapid diagnostic tests to assist in the early diagnosis of herpesvirus infections.

Various tests are presently available for the diagnosis of HSV infections. Most involve the detection of viral antigens or intact infectious virus. Antigen detection assays offer the advantage of rapidity and specificity, but can lack the necessary sensitivity. Kowalski, R. P. and Gordon, Y. J., *Ophthal.* 96:1583–1586 (1989). The most reliable test to detect infectious herpesvirus involves inoculation of specimens onto tissue culture cells followed by detection of infectious virus by microscopically observing a characteristic cytopathic effect. Although HSV is a relatively easy virus to culture as it replicates on a wide variety of continuous cell lines, virus propagation in tissue culture can be slow and expensive. Recently, improved techniques have been developed for the detection of viruses from clinical specimens. The shell vial technique, for instance, has greatly increased the sensitivity and the rapidity of HSV detection. When this method is combined with antigen detection by immunohistochemistry, HSV can be positively identified within 24 hours in the majority of cases. Gleaves et al., J. Clin. Micro. (1985) 21:29–32; Ziegler et al., J. Clin. Micro. (1985) 26:2013–2017. While this type of assay is preferred in diagnostic virology applications, it is labor intensive and a significant number of specimens are not identified as positive until after 48 hours. Another recent technological advance, polymerase chain reaction (PCR) technology, presents a promising tool for the detection of HSV particularly in cerebrospinal fluid specimens, but this technology detects viral nucleic acid and not infectious virus. Puchhammer-Stockl, et al., J. Med. Virol. (1990) 32:77–82. The detection of infectious virus is often preferred because it definitively indicates that there is an ongoing viral infection with active viral replication. PCR detection of viral nucleic acid may only be indicative of the presence of a remnant of a past infection or the presence of a latent infection.

Previous scientific studies involving herpesviruses have used susceptible cell lines transfected with a chimeric DNA construct containing a marker gene in transient assays to study various aspects of the virus such as the regulation of gene expression during viral replication. Flanagan W. M. and Wagner, E. K., Virus Genes 1:1:61–71 (1987). These studies have not, however, described a DNA construct stably integrated into the chromosome of a stable cultured cell line which is suitable for the diagnostic detection and quantification of a herpesvirus in a specimen with the requisite sensitivity and specificity for a clinical diagnostic assay.

Recently, a method for detecting infectious HIV in a specimen has been disclosed that utilizes a genetically engineered cell line containing a chimeric gene having the *E. coli* LacZ gene associated with the HIV-1 LTR promoter. Rocancourt, et al., J. Virol. (1990) 64:2660–2668; Kimpton, J. and Emerman, M., J. Virol. (1992) 66:4:2232–2239. Although these cell lines may be useful for detecting HIV in a specimen, they are not suitable for diagnostic virology assays because of their lack of specificity. It is well-known that the HIV-1 LTR promoter used in the DNA construct of these studies to cause expression of the reporter gene is not specific for HIV and that other viruses cause expression of the reporter gene if present in the specimen. In particular, the presence of HSV or cytomegalovirus in the specimen causes activation of the LTR promoter and subsequent expression of the reporter gene even in the absence of HIV in a specimen. Mosca, J. D., et al., Nature (1987) 325:67–70; Mosca, J. D., et al., Proc. Natl. Acad. Sci. (1987) 84:7408–7412; Popik and Pitha, Proc. Natl. Acad. Sci. (1981) 88:9572–9577. If such a cell line were used in a diagnostic assay, it could lead to the erroneous diagnosis of the presence of HIV in a specimen when in fact the specimen contained a different virus. Thus, the lack of specificity in cell lines prepared to detect HIV in a specimen prevents their use in a diagnostic assay which requires specificity.

A need exists, therefore, for a method for detecting a herpesvirus in a specimen that provides rapid detection in a cost efficient manner, while also providing the sensitivity and specificity necessary for a diagnostic assay.

SUMMARY OF THE INVENTION

The present invention provides a novel assay for detecting the presence of an infectious herpesvirus in a specimen. The assay provides an enzymatic means for identifying the presence of a herpesvirus that can be visually observed or easily detected. The assay involves inoculating a DNA-transfected cell line with a specimen suspected of containing a herpesvirus, allowing a sufficient period of time for the herpesvirus infectious cycle to proceed, and detecting and quantifying the number of herpesvirus-infected cells to determine the number of infectious herpesvirus virions in the specimen. The cell line used in the assay is genetically engineered to express a reporter gene only if infectious herpesvirus is present in the specimen. In certain embodiments of the present invention, the assay is capable of reliably quantifying the number of herpesvirus in a specimen and is so sensitive that it is capable of detecting the presence of a single virion in a specimen.

In another embodiment, the invention provides a novel cell line for use in the assay. The cell line is a DNA-transfected cell line susceptible to infection by a herpesvirus which is stably transformed with a chimeric gene comprising a herpesvirus inducible promoter and a gene coding for an enzyme, the expression of the enzyme being dependent upon and quantitatively proportional to the presence of herpesvirus. In one preferred embodiment, the cell line is a stable baby hamster kidney cell line the genome of which has been engineered to contain the E. coli LacZ gene behind (3' to) an inducible HSV promoter, the HSV-1 ICP6 promoter or the HSV-2 ICP10 promoter. In a second preferred embodiment, the cell line is a stably transformed mink lung cell in which the LacZ gene reporter gene is under the control of a HCMV beta promoter, the UL45 promoter. In other preferred embodiments, the LacZ gene of the above chimeric constructs is replaced with the gene encoding firefly luciferase.

In a further embodiment, the invention provides a kit for assaying the presence of an infectious herpesvirus in a specimen. The kit includes a supply of DNA transfected cells susceptible to infection by the desired herpesvirus being assayed for and engineered to contain a reporter gene, which codes for an enzyme that can be easily detected, behind an inducible herpesvirus promoter, and the reagents necessary to detect expression of the enzyme.

Among the several advantages of the present invention may be noted the provision of a rapid and sensitive assay for detecting the presence of an infectious herpesvirus in a clinical specimen that is suitable as a diagnostic assay; the provision of such an assay that provides reliable results within 12 hours; the provision of such an assay that is adaptable for use as an automated assay; the provision of such an assay that is highly specific for a particular herpesvirus; the provision of such an assay that is capable of detecting a single infectious virion in a specimen; and the provision of a cell line for use in such assay that expresses a reporter gene only after infection with a herpesvirus and not after infection by other viruses.

BRIEF DESCRIPTION OF THE DRAWINGS

FIG. 10 illustrates the cloning of the UL45 gene, showing a schematic representation of the human cytomegalovirus (HCMV) genome including a partial restriction map of the genomic region containing the UL45 gene (FIG. 10A); and showing the UL45 gene cloned into pBR322 (FIG. 10B).

FIG. 13 shows the DNA sequence of the chimeric UL45 promoter:LacZ gene and the predicted amino acid sequence of the fusion product containing 59 amino acids of the UL45 protein fused to the amino terminus of β-galactosidase (SEQ ID NO:4).

FIG. 20 is a list of beta genes in human herpesviruses.

DESCRIPTION OF PREFERRED EMBODIMENTS

Figure 1:
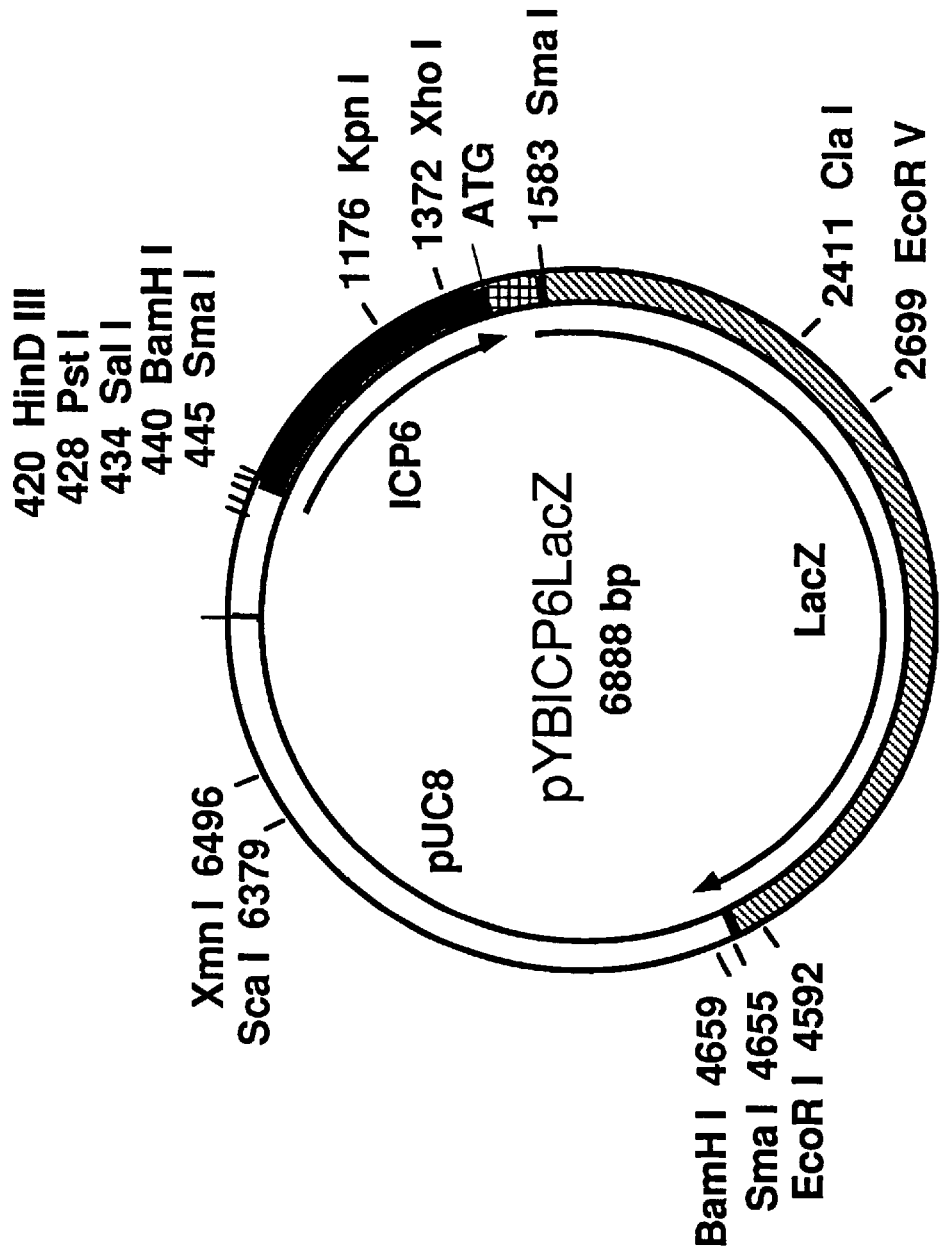
FIG. 1 is a schematic representation of pYBICP6LacZ.

In accordance with the present invention, a method for detecting infectious herpesvirus in a specimen and a provided. The method involves, in one significant respect, an enzymatic assay by which the presence of herpesvirus in a specimen can be detected and quantified in a manner suitable for use as a diagnostic assay. The method employs a genetically engineered cell line containing a stably integrated chimeric gene that permits the detection of the presence of herpesvirus in a specimen. In general, the chimeric gene comprises a transcriptional initiation region from a herpesvirus and a structural gene encoding an enzyme or reporter protein operably coupled thereto such that the transcriptional initiation region regulates the expression of the gene. After inoculation with a herpesvirus, the cell expresses detectable levels of the enzyme.

The genetic elements of the chimeric gene operate as a functional genetic unit to express the enzyme under the control of the transcriptional initiation region, or promoter. The promoter used in the chimeric gene is one that is capable of causing the expression of the structural gene only in the presence of an infectious herpesvirus. Thus, the enzyme is expressed only if an infectious herpesvirus is present in the specimen being analyzed. As used herein, the term infectious herpesvirus denotes herpesvirus virions that are capable of entering cells and initiating a virus replication cycle, whether or not this leads to new virus production.

The promoter is preferably an inducible or transactivatable promoter isolated from the herpesvirus genome. An inducible or transactivatable promoter as used herein is a transcriptional initiation region of DNA that initiates transcription of a DNA sequence operably coupled thereto in response to a transactivating substance produced by the virus. Any inducible or transactivatable promoter from a herpesvirus desired to be detected by the assay may be used in connection with the chimeric gene of this invention. In particular, promoters from herpesvirus β-genes are preferred for use as the promoter in this invention because of their ability to be transactivated. Examples of such herpesvirus beta genes include the genes listed in FIG. 20.

A particularly useful β-promoter is that isolated from Herpes simplex virus type 1 gene UL39, which codes for ICP6 (the promoter being hereinafter referred to as the ICP6 promoter or when used in the identification of vectors and transformed cells, ICP6). The ICP6 promoter is strongly transactivated by the HSV virion-associated transactivator protein VP16 and expression can typically be detected within 3–6 hours after infection by HSV. Moreover, the ICP6 promoter does not cause constitutive expression in uninfected cells, and only causes expression of a gene operably coupled thereto in response to infection by a herpesvirus. This feature of the ICP6 promoter is particularly useful as it provides the specificity required of a useful diagnostic assay.

In general, promoters useful in this invention should not cause constitutive expression in cells that have not been infected by the particular herpesvirus from which the promoter was obtained. The term "nonconstitutive" means that in cells stably transformed with the promoter-reporter gene construct, the reporter gene is not expressed or is expressed at a level that is not practically detectable above background levels by the particular diagnostic assay being used when infectious herpesvirus is not present in the sample being assayed or when the cell infected by the herpesvirus does not contain the reporter gene.

One embodiment of the present invention utilizes a promoter sequence isolated from a gene containing a DNA sequence encoding a ribonucleotide reductase or subunit of a ribonucleotide reductase. In one preferred embodiment of the present invention, the promoter of a HSV-1 UL39 gene that encodes a ribonucleotide reductase large subunit (ICP6) is operably coupled to a reporter gene. In another preferred embodiment of the present invention, the promoter of a HSV-2 gene that encodes a ribonucleotide reductase large subunit (ICP10) is operably coupled to a reporter gene.

The present invention can also utilize a promoter of a gene that corresponds to a UL39 gene of a Herpes Simplex Virus Type 1. The herpesvirus from which the gene is obtained can be any member of the herpesvirus family, and particularly, HSV-1, HSV-2, HCMV, VZV, EBV, HHV6, HHV7, or HHV8. By the term "a gene that corresponds to a UL39 gene of a Herpes Simplex Virus Type 1" it is meant that the gene encodes an amino acid sequence that is a ribonucleotide reductase or subunit of a ribonucleotide reductase and the amino acid sequence is optimally aligned to the amino acid sequence encoded by a UL39 gene. The optimal aligning of amino acid sequences can be determined by standard computer analyses according to identity of amino acids in the sequences as well as physio-chemical and biological similarities of nonidentical amino acids (Nikas et al. INS: Structure, Function, and Genetics 1:376–384, 1986 which is incorporated by reference).

The identification and preparation of DNA sequences containing other beta promoters or promoters corresponding to the ICP6 promoter in other herpesvirus family members can thus be accomplished by using methods that are routine in the art. As noted above, all of the other human herpesviruses contain a DNA sequence encoding a ribonucleotide reductase large subunit and upstream of these DNA sequences are the promoter regions that initiate transcription. Therefore, an approach such as reported by Nikas et al. can be used to identify the DNA sequence in a given herpesvirus family member corresponding to a UL39 gene.

Isolation of the promoter of a gene corresponding to a UL39 gene is exemplified in the isolation of the HSV-2 promoter for the DNA sequence encoding ICP10. The large subunit of ribonucleotide reductase designated as ICP10 in HSV-2 and ICP6 in HSV-1 is encoded within the UL region of the viral genome (map units 0.554 to 0.584). (Wymer et al. *J Virol* 63:2773–2784, 1989; Nikas et al. *PROTEINS: Structure, Function, and Genetics* 1:376–384, 1986 which is incorporated by reference). One method for isolating the promoter for the DNA sequence encoding ICP10 is by PCR amplification of an approximately 600 bp fragment extending from approximately −500 bp to approximately +100 bp relative to the site of transcription initiation. The template for isolating the ICP10 promoter is obtained from cells infected with HSV-2 and primers are synthesized according to the reported sequence for the ICP10 promoter (Wymer et al. supra, at 2779). An approach similar to that outlined above can be used in identifying and isolating the promoters for genes encoding ribonucleotide reductase in other herpesvirus family members utilizing the known DNA sequences of the herpesvirus family members.

In earlier work, Wymer et al. (supra, 1989) cloned a chimeric ICP10 promoter-chloramphenicol acetyltransferase gene construct into Vero (African green monkey) cells as well as into rat astrocytes, a human adenovirus-transformed cell line and a human laryngeal carcinoma cell line. The cells were used in a transient expression assay system and were not stably transformed. This group reported that ICP10 behaves like an immediate-early gene inasmuch as the ICP10 promoter was shown to be stimulated by cotransfection with DNA that encodes a virion protein previously shown to transactivate immediate-early genes.

Other beta promoters particularly useful in the invention are the promoters for the UL45 and UL57 genes of human cytomegalovirus. The UL45 gene corresponds to the HSV UL39 gene and is encoded within map units 0.2 to 0.3 of the $U_L$ region of the HCMV genome (Chee et al., *DNA Seq* 2:1–12, 1991, GenBank Accession No.: X17403). The UL57 gene is a homolog of the UL29 gene of HSV and encodes the 57th ORF in the unique long region of the HCMV genome. One method for isolating the promoters for these beta genes is by cloning into a vector a restriction fragment of the HCMV genome which contains about 500 base pairs of DNA upstream of the coding region of the gene and about 100 base pairs of the coding region. The restriction enzyme (s) suitable for digesting HCMV genomic DNA may be chosen by analysis of the reported sequence for the HCMV genome.

The chimeric gene also includes a structural gene which codes for an enzyme or other protein which serves as a reporter gene product for the visual detection of a herpesvirus in a specimen. The reporter gene product is preferably one that can easily be assayed for or detected in a cell. One enzyme that has proved to be particularly useful as a reporter gene product is β-galactosidase. Preferably, a bacterial β-galactosidase is used, and most preferably the β-galactosidase from *E. coli* that is encoded by the LacZ gene. β-galactosidase is preferred because of its well-characterized nature and the existence of a variety of methods to detect its presence. Other reporter gene products useful in this invention generally include hydrolases or oxidoreductases and, in particular, such enzymes as β-glucosidase, β-glucuronidase, β-hexosaminidase, luciferase, phospholipase, phosphatase, etc. Green fluorescent protein (GFP) is another reporter gene product useful in the invention. The chimeric gene also includes a termination signal which may be integral with and native to the structural gene or may be obtained from a heterologous source.

A gene encoding β-galactosidase is one preferred reporter gene for use in this invention because of the numerous methods known to detect its expression and the relative sensitivity of such methods. Among these methods include histochemical assays involving a chromogenic or fluorogenic substrate which permits detection of β-galactosidase activity by a change in the color of the cell. The change in color can be detected macroscopically or microscopically. For example, in the presence of the chromogenic substrate 5-bromo-4-chloro indolyl-β-D-galactopyranoside, cells producing β-galactosidase will turn blue. Other suitable calorimetric assays use a fluorogenic substrate such as fluorescein di-β-D-galactopyranoside (FDG), 3-carboxyumbelliferyl-β-D-galactopyranoside, or 5-dodecanoylaminofluorescein di-β-D-galactopyranoside ($C_{12}$ FDG) which will stain β-galactosidase-producing cells intensely green. Automated colorimetric assays are also available for detection of β-galactosidase activity. One such assay involves adding to cell lysates o-nitrophenyl galactoside (ONPG) as the β-galactosidase substrate and detecting the yellow o-nitrophenol product by spectrophotometry. Another spectrophotometric assay suitable for use in the invention employs chlorophenol-red-galactopyranoside (CRPG) which is hydrolyzed by β-galactosidase to produce a soluble red product. An automated fluorescence assay is also known.

The detection of β-galactosidase by a fluorescence microscopy method, as further described in Example 9, in the assay of the present invention is advantageous for a variety of reasons. FDG is relatively impermeable to cells and previously described protocols for delivery of FDG into cells involve osmotic shock in addition to careful temperature regulation and the use of competitive and noncompetitive inhibitors of β-galactosidase. These and other complications are necessary for quantitative enzymatic measurements. To detect HSV-infected cells by the method of this invention, however, all that is required is that sufficient FDG enter the cells for the virus-induced β-galactosidase to cleave sufficient FDG to release sufficient fluorescein to allow the cells to be brightly fluorescent. It may be that HSV-infected cells are more permeable to FDG than uninfected cells. In addition, the fact that BHK cells have little in the way of endogenous β-galactosidase activity or autofluorescence, and the fact that no constitutive β-galactosidase activity has been observed in cells of the present invention, results in virtually no background fluorescence in uninfected cells. The combination of all these factors contribute to the high signal to noise ratio (i.e. easy visual discrimination between infected and uninfected cells) despite a simple method to deliver the FDG to the cells.

Previously described procedures to detect β-galactosidase positive cells using fluorogenic substrates involved cooling the cells below the membrane freezing point after exposure to the fluorogenic substrate to prevent fluorescein from diffusing out of the cells. This adds a complication to the fluorescence microscopy (i.e. it would require a cooling chamber on the microscope) which was found not to be necessary when this means for detection was used with the method of this invention. The cells can be held at ambient temperatures so long as the cells are observed within 15 minutes from the time of exposure to the FDG without loss of sensitivity.

Another particularly useful reporter gene for use in the method and cell line of this invention is the gene encoding firefly luciferase. The expression of luciferase may be detected by known luminometric methods using luciferin as the enzyme substrate. The use of luciferase as the reporter gene provides an enzymatic assay that is more sensitive than the colorimetric or fluorometric β-galactosidase assay and is also more amenable to the development of an automated assay which can detect a single infectious virus.

Once the desired chimeric gene has been prepared, it is preferably inserted into a plasmid which is then stably transformed into the desired cell line by standard and routine methods known to those skilled in the art. Maniatis, T., et al., Cold Spring Harbor, N.Y. Cold Spring Harbor Laboratory (1990). The cell line chosen is one that is susceptible to infection by the herpesvirus to be detected and is transfected in a manner that stably integrates the chimeric gene into a chromosome of the cell. A cell line is susceptible to infection if the infecting virus can enter the cell and proceed far enough in its replication cycle to express beta genes. Susceptible cell lines for herpesviruses include rabbit skin fibroblasts, baby hamster kidney cells, African green monkey cells, mink lung cells, and the like. It will be understood by those skilled in the art that cell lines susceptible to infection by a particular herpesvirus family member can be readily identified by searching the literature for known susceptible cell lines or by screening candidate cell lines using well-known procedures requiring only routine experimentation. For example, parameters important for predicting cell lines permissive for HCMV infection are discussed in Smith, *J. Virol.* 60:583–388, 1986, incorporated herein by reference.

One preferred cell line for the detection of HSV in a sample comprises baby hamster kidney cells into whose genome has been stably integrated a chimeric gene comprising the *E. coli* LacZ gene behind the HSV-1 ICP6 promoter, and, in particular, a cell line identified as BHKICP6LacZ and clones thereof. Another preferred cell line for the detection of HSV in a specimen comprises baby hamster kidney cells into whose genome has been stably integrated a chimeric gene comprising the firefly luciferase gene behind the HSV-1 ICP6 promoter, and, in particular, a cell line identified as BHKICP6LucA6 and clones thereof.

Another preferred cell line for the detection of HSV in a sample comprises baby hamster kidney cells into whose genome has been stably integrated a chimeric gene comprising the E. Coli LacZ gene behind the HSV-2 ICP10 promoter, and, in particular a cell line identified as BHKICP10LacZ and clones thereof.

For the detection of HCVM in a sample, a preferred cell line comprises a mink lung cell line into whose genome has been stably integrated a chimeric gene comprising the E. Coli LacZ gene behind the HCMV UL45 promoter, and, in particular, a cell line identified as MLUL45LacZ and clones thereof. Another embodiment of a cell line for detecting HCMV comprises the chimeric UL45 promoter-lacZ gene stably transformed into the genome of a baby hamster kidney cell line.

In order to detect the presence of an infectious herpesvirus in a specimen, a cell line that has been transfected with a chimeric gene as described above is inoculated with the specimen by placing an aliquot of each in a suitable standard culture medium in standard culture vessels. The specimen may be any material which can be placed into a fluid or fluid from a person, animal or the environment such as blood, semen, nasopharyngeal swabs, cerebrospinal fluids and the like. The cell line and the specimen are cultured for a sufficient period of time for the herpesvirus infectious cycle to proceed. Typically, this takes between three and twelve hours and usually between three and six hours. If an infectious herpesvirus is present in the specimen, it will produce the transactivator necessary to induce the promoter and cause the expression of the marker gene which can then be detected and quantified by assaying for the presence of the reporter gene product. This method enables one to determine whether a certain specimen contains an infectious herpesvirus.

In another embodiment of the assay, one or more inducers of viral gene expression and/or replication are added to the stably transformed cells either before and after infection by the herpesvirus or added only after infection. Such inducers are known in the art. For example, retinoic acid has been shown to induce HCMV replication in undifferentiated human embryonal carcinoma cells (Gonczol et al., *Science* 224:159–161, 1984, incorporated herein by reference), and replication of several herpesviruses, including HCMV, was induced in some, but not all, nonpermissive cell types by 5-iodo-2'-deoxyuridine (IDU) (Smith et al., *J. Virol.* 60:583–588, 1988; St. Jeor et al., *J. Virol.* 11:986–990, 1973, which are incorporated herein by reference). In addition, it has been shown that HSV synthesis can be induced in mouse neuroblastoma cells by $C_2$–$C_5$ fatty acids, i.e., propionate, butyrate, and valerate (Ash, *Virology* 155:584–592, 1986, incorporated herein by reference). Sodium butyrate (NaB) has also been shown to induce HCMV replication in human endothelial and epithelial cells (Radsak et al., *Arch. Virol.* 107:151–158, 1989; Tanaka et al., *Virology* 185:271–280, 1991, which are incorporated herein by reference).

The method and cell line of this invention may be used to detect infectious herpesviruses such as Epstein-Barr Virus, Cytomegalovirus, Varicella-Zoster Virus, and the Herpes Simplex Viruses. In particular, this invention is useful for the detection of infectious HSV or CMV in a clinical specimen.

The following examples are offered by way of illustration and not by way of limitation.

EXAMPLE 1

This example illustrates the preparation of a susceptible cell line genetically engineered to enable it to detect infectious herpes simplex virus.

Baby hamster kidney (BHK-21) cells were obtained from C. Hahn and C. Rice (Washington University, St. Louis, Mo.). The cells were propagated in MEM medium (Gibco-BRL, Gaithersburg, Md.) supplemented with 7% fetal calf serum (Gibco). These cells were co-transfected with pYBICP6LacZ and pMAMneo by the liposomal transfection protocol as described in Maniatis, T., et al. (1990) using reagents obtained from Gibco-BRL. The essential features of plasmid pYBICP6LacZ are shown in FIG. 1. This plasmid was prepared by isolating a BamHI fragment from pD6p, obtained from Dr. Sandra Weller (Univ. of Conn.), which contains the ICP6-LacZ fusion cassette as described in Goldstein and Weller, *J. Virol.* 62:196–205 (1988), and subcloning this fragment into the BamHI site of the vector pUC8. Plasmid pMAMneo contains the SV40 early promoter-neomycin resistance gene cassette and was purchased commercially from Clontech, Palo Alto, Calif.

The transfected cells were placed in a culture medium containing G418 (geneticin, Sigma, St. Louis, Mo.) and G418 resistant colonies were selected. Several cell lines were identified as being resistant to G418 and were tested for β-galactosidase activity. One such cell line, BHKICP6LacZ-5, displayed no detectable β-galactosidase activity after mock infection and pronounced activity following infection with HSV. This cell line was selected for further studies.

EXAMPLE 2

This example illustrates the ability of the cell line of this invention to detect infectious herpes simplex virus in a specimen.

Cells from cell line BHKICP6LacZ as described in Example 1 were obtained and infected with HSV-1 at various multiplicities of infection (m.o.i.) in standard tissue culture medium. The cells and the virus were allowed to remain in culture for 12 hours after which the cells were assayed for β-galactosidase activity by the histochemical staining method. The cells were washed three times in phosphate buffered saline (PBS) pH 7.2 and fixed in a solution of 2% formaldehyde and 0.4% glutaraldehyde in PBS for 5 minutes at 4° C. The cells were then washed twice in PBS and incubated for 2 hours at room temperature in the histochemical staining solution. The solution comprises 1 mg/ml X-GAL (5-bromo-4-chloro-3 indolyl-β-D-galactopyranoside), 4 mM potassium ferricyanide, 4 mM potassium ferrocyanide, 2 mM $MgCL_2$ in PBS. The staining solution was made up fresh before use with concentrated stock solutions of each reagent. The X-GAL stock solution was 40 mg/ml in N, N-dimethylformamide. The reaction was stopped by washing the cells with PBS. The cells were analyzed directly and by light microscopy and stored in PBS at room temperature.

At the higher m.o.i., the blue stain was evident macroscopically and as the m.o.i. decreased, microscopic examination of the cells which did not appear to stain blue by direct inspection revealed individual blue cells among a predominance of unstained cells. Microscopic analysis of the infected cells revealed blue stained cells. Control cells subject to no infection and mock infection exhibited no blue staining of the cells.

EXAMPLE 3

This example illustrates the ability of the cell line and assay of this invention to quantitate the number of infectious herpes simplex virus particles in a specimen.

Herpes simplex virus is routinely quantified by determining the titre of infectious virions as plaque forming units (pfu) per milliliter (ml). A solution known to contain herpes simplex virus, but of unknown amount, was submitted to a standard quantitative plaque assay. An aliquot (0.5 ml) of the solution was placed into a tube with 4.5 ml of culture medium constituting a 10-fold dilution. This diluted sample was then diluted 10-fold in like manner serially until a 10,000,000 dilution was achieved in the final tube. We now had tubes with $10^{-1}$ through $10^{-7}$ the concentration of virus of the original solution. An aliquot (0.5 ml) of the highest three dilutions ($10^{-5}$, $10^{-6}$, $10^{-7}$) was added to a monolayer of BHK cells in 10 cm$^2$ wells. This was done in duplicate. After allowing the virus to absorb to the cells for one hour, the media was aspirated from the well and replaced with media containing neutralizing antibody to herpes simples virus (to restrict spread of the virus to a focal area of the monolayer). After 48–72 hours circular areas of dead cells (plaques) appeared in the monolayer. The number of plaques in each well was counted. Wells with too many plaques (>100) or too few plaques (<10) were not counted. In one assay, 21 plaques were seen on one of the duplicate wells using the $10^{-7}$ dilution and 17 plaques on the other duplicate. The titre of the starting solution was then calculated using the following formula:

average # plagues/well×1/volume added to cells=pfu/ml dilution

Therefore in the above case the average # of plaques= 17+21/2=19. The dilution was $10^{-7}$. The volume added was 0.5 ml.

The title was therefore $$\frac{19}{10^{-7}} \times 1/0.5 = 38 \times 10^7 \text{ or } 3.8 \times 10^8$$

The same exact dilutions were also inoculated onto BKHICP6LacZ-5 cells in exactly the same manner except that after 16 hours the cells were fixed and histochemically stained for β-galactosidase activity (16 hours is less than growth cycle of herpes simplex virus and thus too short a time period for a plaque to form). Blue cells were then counted in each well with an inverted light microscope. In duplicate wells derived from the $10^{-7}$ dilution, 20 and 23 blue cells were seen. A blue cell is referred to as a blue forming unit (bfu) and the number of bfu per ml was calculated using the same formula as above:

$$\text{average \# blue cells} = \frac{20+23}{2} = 21.5$$

$$\text{bfu/ml} = \frac{21.5}{10^{-7}} \times 1/0.5 = 43 \times 10^7 \text{ or } 4.3 \times 10^8$$

In summary, a virus containing solution was diluted and the identical dilutions were submitted to the standard assay to quantitate infectious herpes simplex virus and to the histochemical assay using BHKICP6LacZ cells and the calculated number of plaque forming units per ml closely approximated the number of bfu per ml. The titres (3.8×10$^8$ pfu/ml and 4.3×10$^8$ bfu/ml) are essentially equivalent from a virologic point of view given the intrinsic variability of a quantitative plaque assay. Therefore, as a pfu is used as an indicator of a single infectious virus, a bfu also can also be used as an indicator of a single infectious virus.

EXAMPLE 4

This example illustrates the ability of the assay of this invention to rapidly detect HSV-1 in a specimen.

Figure 2:
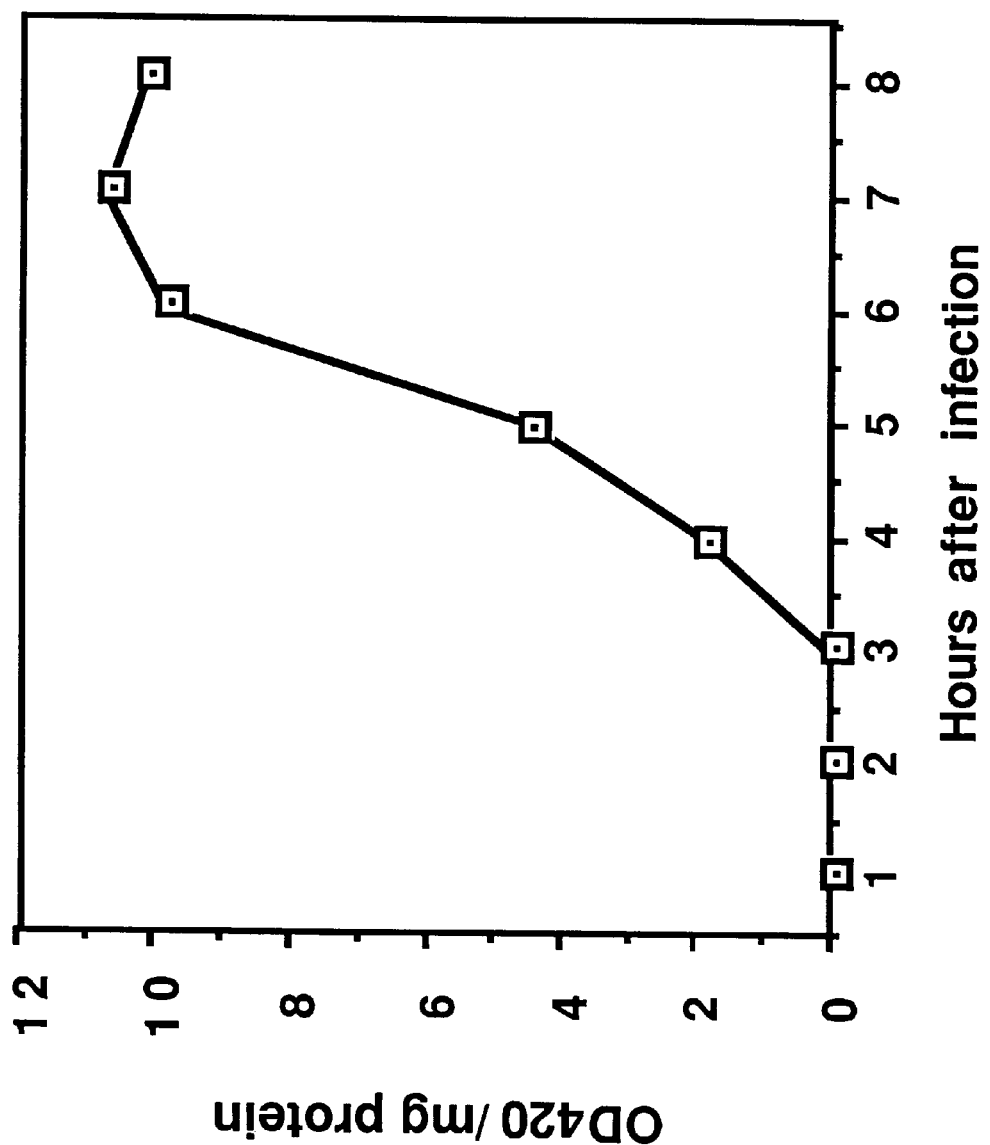
FIG. 2 is a graphical representation of β-galactosidase activity in Herpes Simplex Virus-infected BHKICP6LacZ cells at various timepoints after infection as measured by a calorimetric assay on cell lysates.

BHKICP6LacZ cells as described in Example 1 were infected with HSV-1 at a m.o.i. of 10 and 0.1 as previously described in Example 2. At various times after the cells were infected, cells were removed, lysed and assayed for β-galactosidase activity by a calorimetric assay. The calorimetric assay was performed on whole cell lysates using O-nitrophenyl-β-D-galactopyranoside (ONPG, Sigma, St. Louis, Mo.) as the substrate in a standard colorimetric β-galactosidase assay as described in Maniatis, et al., Cold Spring Harbor, N.Y., Cold Spring Harbor Laboratory (1990). Protein determinations of the lysates were performed using a commercially available kit based on the Bradford method (Bio-Rad, Richmond, Calif.). Enzyme activity was detected approximately four hours after infection and peaked at six hours after infection for the cells infected at a high m.o.i. FIG. 2 presents a graphical representation of the detection of β-galactosidase activity vs. time by this assay.

As a comparison, cells subject to the same method of infection were assayed by the histochemical staining method as described in Example 2. A few blue staining cells could be seen at approximately three hours after infection and greater than and 90% of the cells stained blue after six hours for the cells infected with a high m.o.i. The cells infected with a low m.o.i. did not develop blue staining cells until approximately six hours after infection.

EXAMPLE 5

This example illustrates the specificity of the cell line and method of this invention to detect only the presence of HSV in a specimen.

Monolayers of BHKICP6LacZ-5 cells were inoculated, separately, with specimens known to contain other viruses and assayed histochemically for β-galactosidase activity. Infection of BHKICP6LacZ cells with four different viruses resulted in no β-galactosidase expressing cells.

Three virus specimens were obtained from the Diagnostic Virology laboratory at St. Louis Children's Hospital. Separate specimens were obtained which contained human cytomegalovirus (HCMV), varicella zoster virus (VZV) and adenovirus type 5. Each of the specimens contained an amount of virus derived from a 4+ cytopathic effect (a semiquantitative measure of the amount of virus in a sample whereby 1+ equals the least amount and 4+ the highest amount). In addition, a laboratory strain of Sindbis virus (a Togavirus) with a titre of $10^7$ pfu/ml was grown in the laboratory. A 0.5 ml aliquot of each of these viruses was separately inoculated onto monolayers of 2.0×10$^6$ BHKICP6LacZ-5 cells. (This amount of each virus when inoculated onto the cell line normally used to grow these viruses resulted in a 4+ cytopathic effect characteristic of each virus). At 24 hours after infection with each of these viruses the BHKICP6LacZ cells were fixed and histochemically stained for β-galactosidase activity. BHKICP6LacZ-5 cells infected with none of the four viruses exhibited any histochemical evidence for β-galactosidase activity i.e. no blue cells were seen microscopically. HSV type 2 infection of BHKICP6LacZ cells resulted in β-galactosidase activity in a manner indistinguishable from HSV type 1. Thus this method is specific for HSV-1 and HSV-2 (collectively HSV).

EXAMPLE 6

This example illustrates the use of the cell line and assay of this invention for analyzing clinical specimens for the presence of HSV.

A prospective study was done in a diagnostic virology laboratory. During the period between Sep. 9, 1991 and Nov.

28, 1991 all specimens the laboratory received for the purpose of detecting HSV were submitted to both the standard cytopathic effect (CPE) assay and the method of this invention. A total of 96 specimens were processed from 94 patients. Specimens were derived from multiple body sites (swabs of cervical, skin, mouth lesions, bronchoalveolar lavage specimens, etc.) All specimens were received in a standard physiologic transport medium.

For the standard CPE assay, a 0.2 ml aliquot of each specimen was inoculated into a roller tube containing a monolayer of a tissue culture cell line (rabbit skin fibroblasts) obtained commercially and commonly used to grow HSV. After one hour on a roller apparatus at 37° C., fresh tissue culture medium (minimal essential medium+5% calf serum) was added and the cells were returned to the roller apparatus and the 37° C. incubator. The following day, and at 12 hour intervals for up to 7 days, the cells were examined microscopically, by a trained diagnostic virology technician using an inverted light microscope, for evidence of CPE characteristic of HSV. The results of this analysis were part of the laboratory's normal diagnostic function and were reported to the physician who ordered the test.

At the same time that the CPE assay was set up another assay using the method of this invention was set up in parallel. A 0.2 ml aliquot of each specimen was also inoculated onto BHKICP6LacZ-5 cells which were being cultured on the exact same type of roller tube used for the commercially purchased cells mentioned above. The cells were processed in the same manner except that on the day after inoculation (16–24 hours depending on when the time of day the specimen was received by the laboratory and done at the convenience of the technician) the cells were fixed and histochemically stained for β-galactosidase activity. The cells were then examined under a light microscope and scored for the presence of blue cells. The results are shown in Table I below.

TABLE 1

| # Specimens | CPE | β-gal. Stain |
|---|---|---|
| 31 | + | + |
| 62 | − | − |
| 0 | + | − |
| 3 | − | + |

As shown by the data in Table 1, all 31 specimens that contained HSV as evidenced by the positive CPE assay were positive in the β-galactosidase staining assay i.e. there were no false negatives. It should be noted that the β-galactosidase staining was done "blindly" i.e. without knowledge of the CPE results. In fact, 15 of the 31 CPE positive specimens did not become positive until day 2 or more. Therefore at the time of the histochemical staining these 15 CPE positives were still read as negative. As can be seen in Table 1, 3 specimens that were read as positive by the technician for β-galactosidase staining were negative by CPE. Two of these were from the same patient and were from an oral source. Examination of the histochemically stained cells revealed that the blue cells were not, in fact, fibroblasts (as are BHKICP6LacZ-5 cells) but obviously epithelial cells. These cells likely came from the patients mouth and the cells likely were colonized with a bacteria expressing β-galactosidase. Consistent with this notion, we repeated the assay on these specimens and noted that these cells stained blue at time zero before HSV would have time to induce β-galactosidase activity. The third specimen that was CPE-negative, β-galactosidase positive displayed a single blue cell whereas all the other 31 positives had many blue cells. This false negative result remains unexplained. No virus (HSV or otherwise) was cultured from this specimen. Finally two of the CPE-negative, β-galactosidase negative specimens grew varicella zoster virus (VZV), confirming our laboratory observation of the specificity of the method of this invention for HSV.

In summary, the method of this invention, when compared to the standard laboratory method to detect HSV on clinical specimens, showed excellent (100%) sensitivity (31/31). It was also more rapid than the standard method in that all 31 positives were detected at 24 hours or less compared to 16 of 31 CPE positives at 24 hours and the remaining 15 not being noted to be positive until 48 or 72 hours.

EXAMPLE 7

This example demonstrates the ability of the firefly luciferase gene to be used as a reporter gene to detect HSV. The rationale for using luciferase is that the enzymatic measurement of luciferase on cell lysates is far more sensitive than β-galactosidase.

Figure 3:
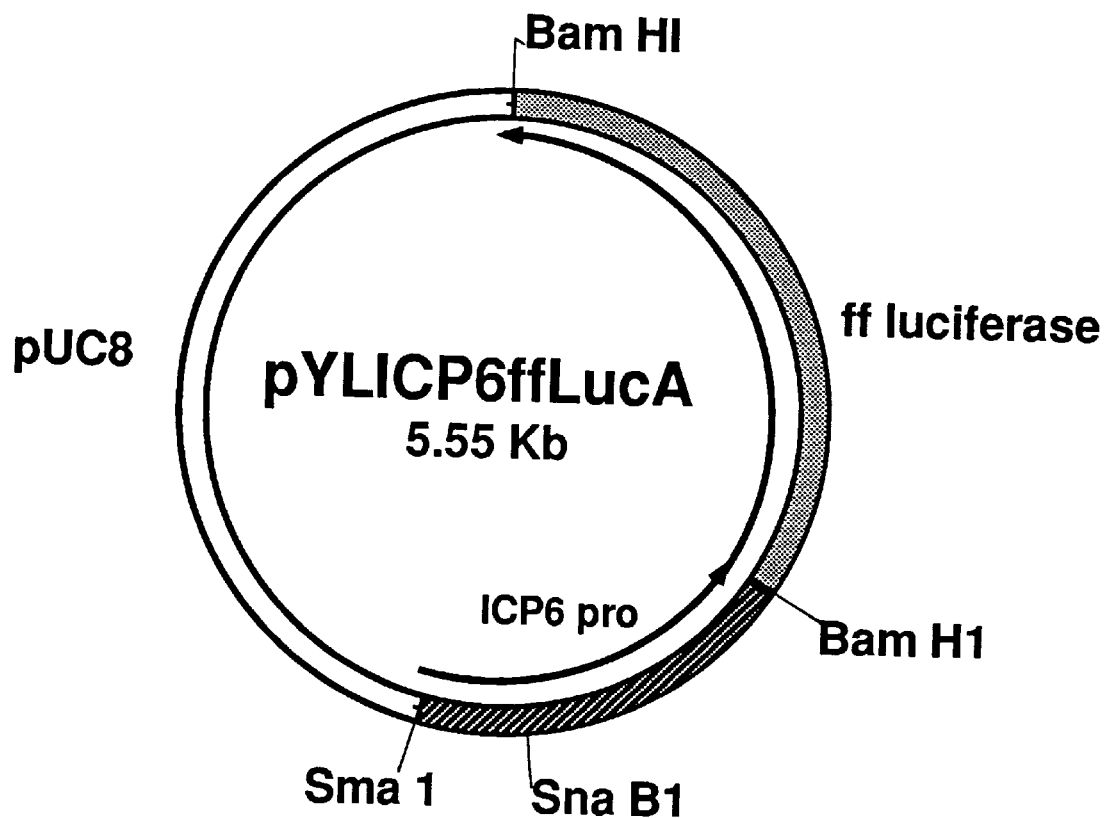
FIG. 3 is a schematic representation of pYLICP6ffLucA.

A cell line was derived from BHK cells using the method described in Example 1. BHK cells were stably transformed with pMAMneo and pYLICP6ffLucA (which contains a ICP6-firefly luciferase chimeric gene), a map of which is shown in FIG. 3, using G418 selection. pYLICP6ffLucA was prepared by inserting a 1.9 kb fragment from pTS/T7Luc (Clontech, Palo Alto, Calif.) which contains the luciferase gene into the BamHI site of pDCICP6-1B which has a BamHI site at the 3' end of the ICP6 promoter. The ICP6:luciferase chimeric gene is not expressed as a fusion protein. One such stably transformed cell line was named BHKICP6LucA6.

Figure 4:
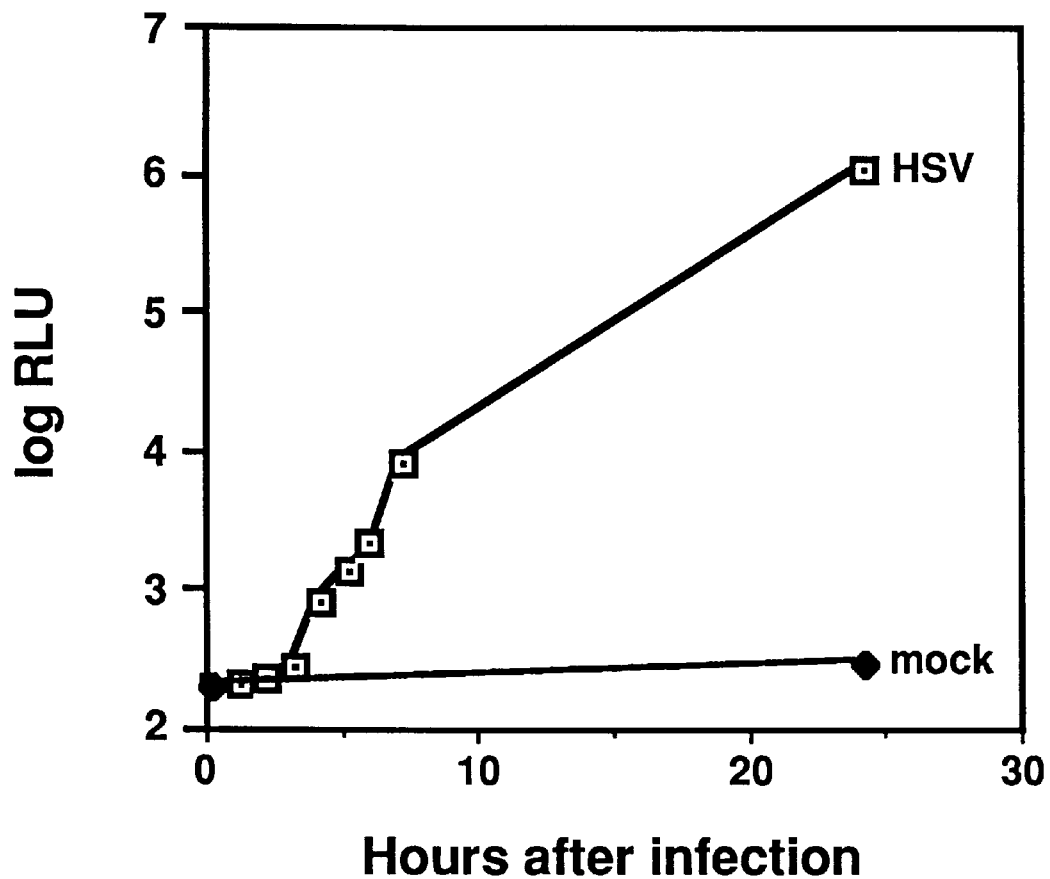
FIG. 4 is a graphical representation of luciferase activity in Herpes Simplex Virus-infected BHKICP6LucA6 cells at various timepoints after infection as measured by luminometry on cell lysates.

BHKICP6LucA6 cells were grown as monolayers on 24 well tissue dishes (2.5–5.0×$10^5$ cells per well). The cells were then infected with $10^3$ pfu of HSV per well. At various times after infection the cells were lysed and assayed for luciferase activity. The procedure was as follows. The media (MEM+10% fetal calf serum) was aspirated, the cells were washed 2× with 1 ml of phosphate buffered saline, pH 7.4, and then 0.1 ml of lysis buffer (50mM Tris-MES pH 7.8, 1 mM DTT, 1% Triton X-100) was added. The dish was placed on a rotating shaker for 10 minutes at ambient temperature. 0.05 ml of each cell lysate was then assayed for luciferase activity in the following protocol. 0.150 ml of luciferase reaction buffer (final reaction concentrations: 50 mM Tris-MES, pH 7.8, 10 mM magnesium acetate, 2 mM ATP) as added to a 12×75 mm disposable glass tube. 0.05 ml of the cell lysate was added and mixed gently. The tube was placed in a luminometer which automatically injects 0.1 ml of 1 mM luciferin and then measures the release of photons over a 10 second period of time. A number is recorded as relative light units (RLU) as a measure of the amount of luciferase activity. Typically 0.05 ml of buffer lacking luciferase, or 0.05 ml of a BHK cell-lysate, gives a value of 150 to 200 RLU in this assay. Uninfected BHKICP6LucA6 cell lysates give 4–8×$10^{-4}$ RLU per cell or 300–400 RLU for a 0.05 ml lysate of 2.5×$10^5$ cells. FIG. 4 shows a time course of luciferase activity after infection of BHKICP6LucA6 cells infected as described above. As can be seen, luciferase activity increases well above uninfected cell background by 4 hours after infection and by 24 hours the luciferase activity is 5000-fold above the uninfected cell background. The data illustrated in FIG. 4 represents $10^3$ infected cells and 2.5× $10^5$ total cells in the assay; the calculated RLU/infected cell to RLU/uninfected cell ratio is at least 500,000.

EXAMPLE 8

This example illustrates the ability of the BHKICP6LucA6 cell line and the method of Example 7 to detect a single infectious HSV in an enzymatic luciferase assay on cell lysates.

BHKICP6LucA6 cells were cultured in 24 well dishes. The cells were inoculated with a solution of diluted HSV. Four dilutions were made with concentrations of virus (based on a predetermined titre done as described in Example 3) of 5 pfu/ml; 2.5 pfu/ml; 0.5 pfu/ml; and 0.025 pfu/ml. 0.2 ml of each of these diluted HSV solutions were then inoculated into 9 separate wells and 6 well were uninfected (i.e. 42 well total). Therefore 6 wells got no virus. 9 wells 1 pfu, 9 wells 0.5 pfu, 9 wells 0.1 pfu, and 9 wells 0.05 pfu. Since an HSV pfu is a discrete entity, these numbers actually represent a certain probability of each well getting infected or not and that probability can be calculated using a standard Poisson equation. The cells were then harvested for luciferase activity as described in Example 7. In parallel these same exact dilutions were inoculated onto BHK cells and microscopically observed daily for CPE for 7 days.

Figure 5:
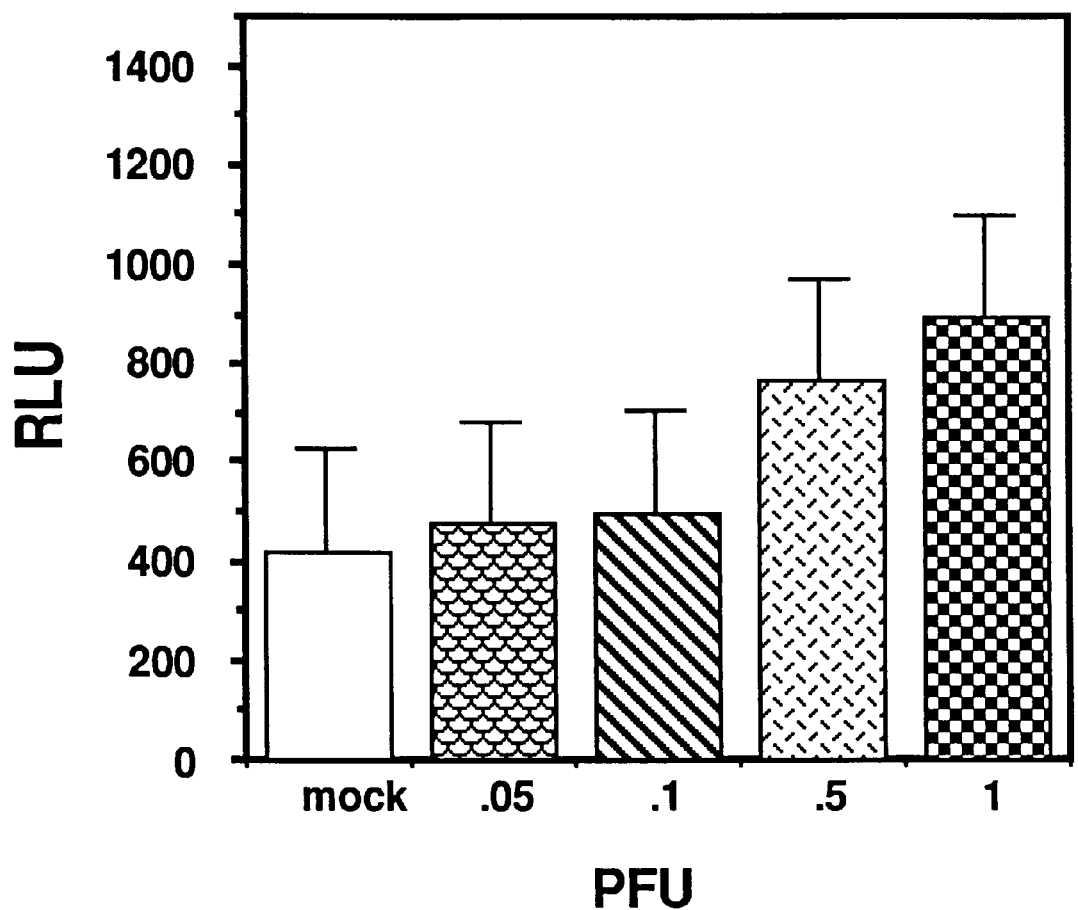
FIG. 5 illustrates the average luciferase activity as a measure of the amount of virus added to an assay.
Figure 6:
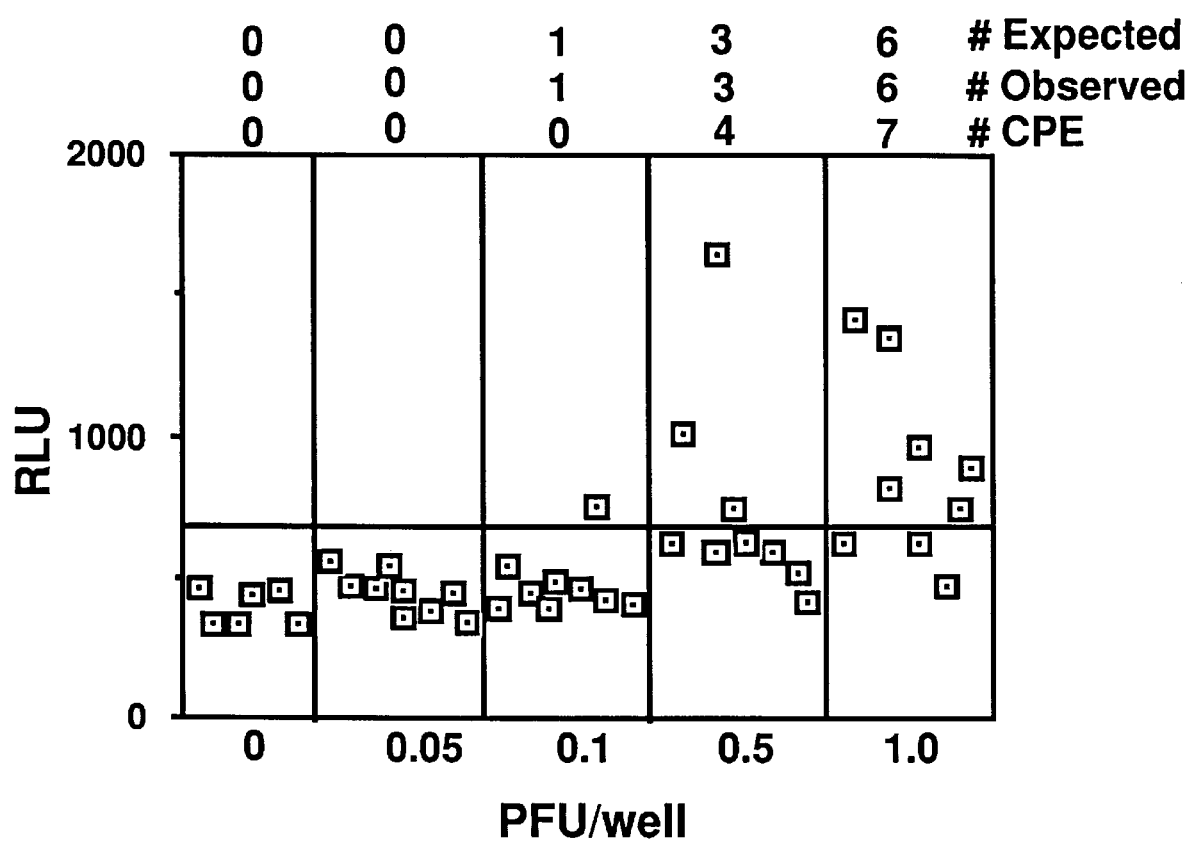
FIG. 6 illustrates the individual data points of luciferase activity used to obtain the average luciferase activity values in FIG. 5.

FIG. 5 shows the average luciferase activity as a measure of the amount of virus added. Although there is a trend toward increased activity with more virus it is not statistically significant. When the individual data points are analyzed (FIG. 6), however, it is clear than an individual pfu can be detected. The # expected equals the number of wells that should receive a PFU based on Poisson probability. The # CPE equals the number of wells in which CPE was seen on the BHK cells. The # Observed equals the number of wells in which the measured luciferase activity was above uninfected cells by an amount predicted to be present in a single infected cell. (This was determined by infecting 3 wells with 100 pfu and the RLU measured from those cells was averaged and divided by 100). There is clearly a good correlation between the Poisson predicted # of infected wells and the # CPE positive wells which shows that our virus titre is accurate. The good correlation between these numbers and the number of wells with higher luciferase activity than the uninfected cell background indicates that this method can detect a single infected cell and thus a single infectious herpes simplex virus.

EXAMPLE 9

This example illustrates the use of the BHKICP6LacZ-5 cell line and the method of this invention to detect HSV-infected cells (and thus infectious HSV in a specimen) by fluorescence microscopy. The advantages of this assay are that it is very rapid (4 hours), very simple to perform, and the cells remain viable, thus allowing the same cells to be analyzed repeatedly over time.

A monolayer of approximately $2\times10^5$ BHKICP6LacZ-5 cells were grown in standard culture medium (MEM+10% fetal calf serum) on a commercially available tissue culture chambers/microscope slide device. The cells in individual chambers were inoculated with between 100 and 1000 pfu of HSV in 0.2 ml of medium, or mock infected with 0.2 ml of sterile medium, and then placed in a 37° C. incubator. In one hour intervals after infection the cells were processed in the following manner. The medium was aspirated and replaced with phosphate buffered saline (PBS) containing 4 mM FDG (fluorescein di-β-galactopyranoside, Molecular Probes, Eugene, Oreg.; cat. no. F-1179). FDG is a fluorogenic β-galactosidase substrate. After one minute at 37° C. the PBS/FDG was aspirated and fresh culture medium was added at ambient temperature. The cells were then observed immediately under an inverted microscope with a fluorescent light source (Zeis Axiovert 35) using the appropriate filters for fluorescein green fluorescence.

Mock infected (i.e. uninfected) cells displayed no visible fluorescence. Infected cells showed no fluorescence at 1 hour and 2 hours after infection. At 3 hours after infection, however, individual cells displayed a low level of fluorescence which increased to a dramatic level of fluorescence at 4 hours after infection. The number of fluorescence positive cells correlated with the number of pfu used in the infection. The fluorescence faded to a faint level over 30 minutes. The cells were placed back in a 37° C. incubator and were reassayed in exactly the same manner at 6, 12, and 16 hours after infection. The same number of fluorescence positive cells were seen at each time point from the 4 to 16 hours.

EXAMPLE 10

This example illustrates the preparation of the ICP10 promoter.

The ICP6 and ICP10 genes show a high degree of sequence homology particularly in the predicted amino acid sequences of the protein which they encode. The DNA sequences containing the promoters of these genes are upstream of the open reading frames of these genes and show a lesser degree of sequence homology. The ICP10 promoter was, therefore, prepared using polymerase chain X reaction (PCR). The PCR primers were made based upon the published ICP10 promoter sequence of HSV-2 strain 333 as described in Wymer et al. (supra, 1989).

The DNA used as the template for the PCR reaction was obtained from Vero cells infected with HSV-2 (strain 333). $2\times10^6$ cells were infected with 0.05 plaque forming units (pfu) per cell ($10^5$ pfu). Three days after infection the media was removed. Viral DNA was isolated from a 100 microliter aliquot by extraction two times with phenol followed by two times with chloroform. The DNA was then precipitated with 2.5 volumes of 95% ethanol. The precipitate was dried and resuspended in 100 microliters of TE buffer (10 mM Tris, 1 mM EDTA, pH 8.0). One microliter was used in the PCR reaction.

Figure 7A:
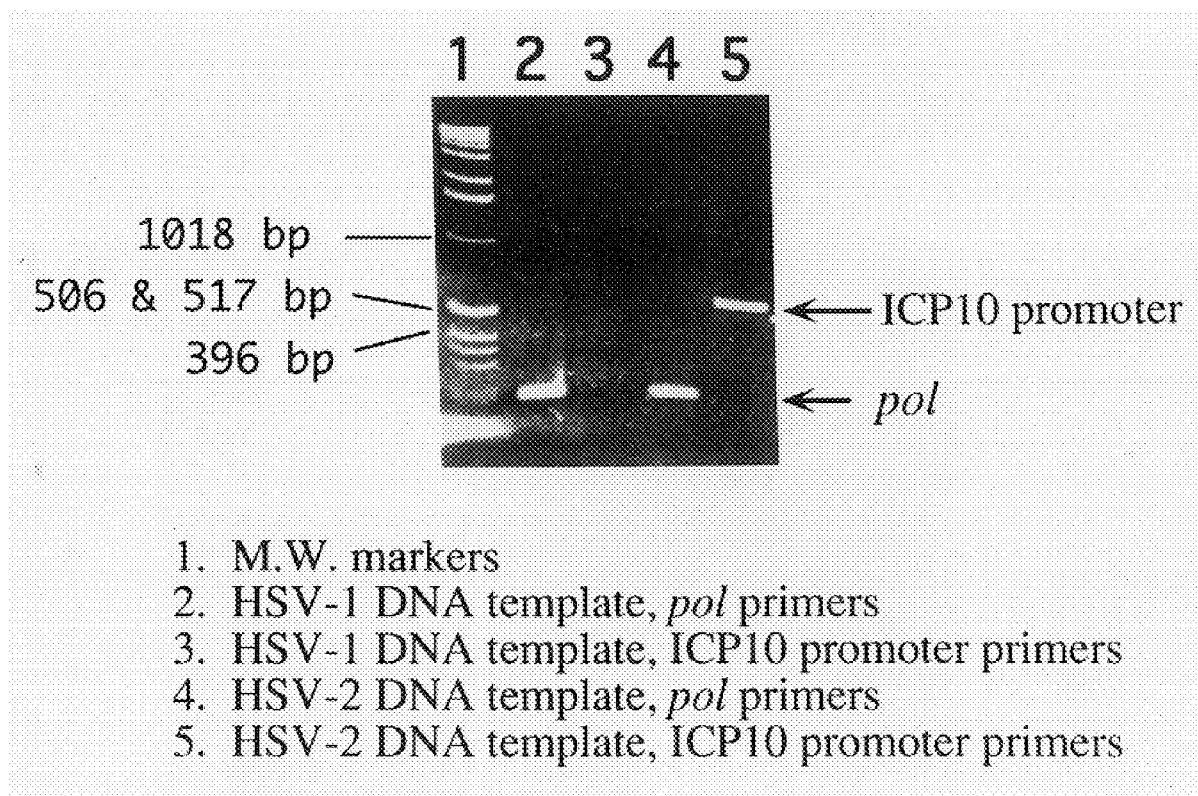
FIG. 7 illustrates (A) The ethidium bromide stained agarose gel electrophoresis of the ICP10 promoter PCR product obtained using ICP10 promoter primers, 5'-GTCATGCCAGACAACAGC-3' (SEQ ID NO:1) and 5'-CCGACAGGAACGCAACAGG-3' (SEQ ID NO:2); and (B) a schematic restriction map of the ICP10 PCR product.
Figure 7B:
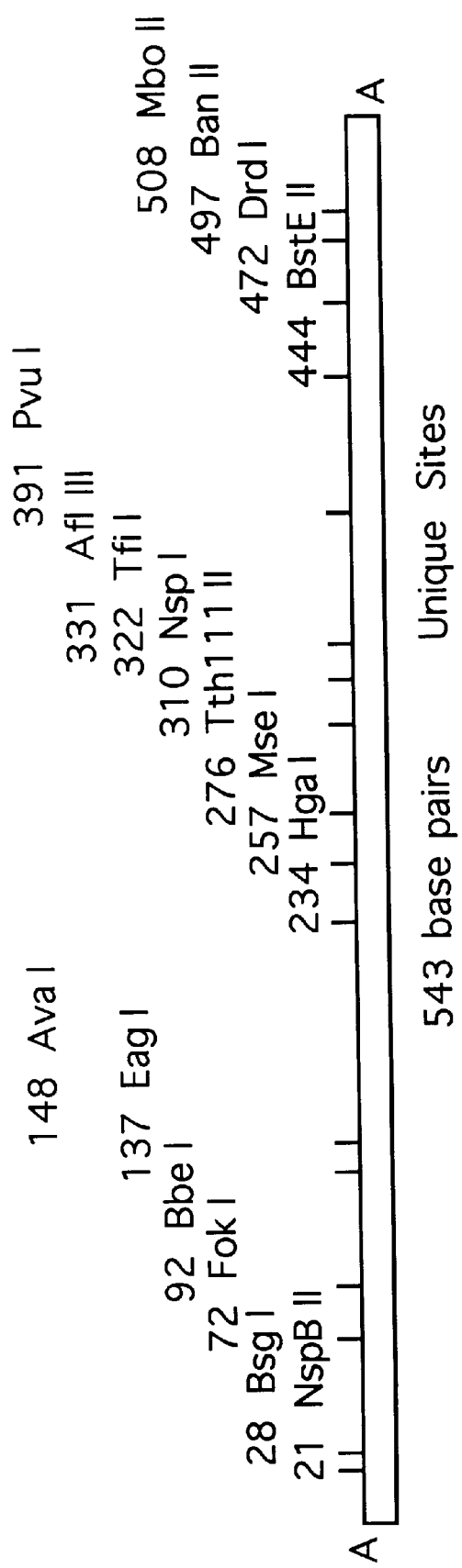

To amplify the ICP10 promoter of HSV-2, a PCR reaction was run with oligonucleotide primers based on the published sequence of the ICP10 promoter from HSV-2 strain 333 (see Wymer et al., 1989 and FIG. 7 therein).

The upstream (5') primer was 5'-GTCATGCCAGACAACAGC-3' and the downstream (3') primer was 5'-CCGACAGGAACGCAACAGG-3'. Using these primers the predicted product would be a 543 bp fragment which extends from −448 to +94 relative to the start of transcription. Id.

PCR employed a Thermocycler 480 (Perkin Elmer Cetus, Norwalk, Conn.) using tag polymerase (Promega, Inc.) and standard techniques, well known in the art. See, for example Saiki, R. K. et al., *Science* 239:487–491 (1988).

The reaction mixture was distilled water, 82 µl; 10× PCR buffer, 10 µl; dNTP mix, 4 µl; primers, 1 µl each; DNA template, 1 µl; Taq polymerase (5 u/µl), 0.5 µl. The samples were run under the following conditions denaturation at 95° C. for 1 minute, annealing at 58° C. for 1 minute, elongation at 72° C. for 1 minute for 35 cycles. Five microliters of the 100 microliter reaction were analyzed by electrophoresis in a 1% agarose gel followed by staining with ethidium bromide. Molecular weight markers were obtained from Gibco/BRL.

Using the ICP10 promoter primers and an HSV-2 (strain 333) DNA template, the PCR reaction amplified the 543 bp fragment. (see FIG. 7, lane 5). Three PCR reaction controls were additionally run. PCR amplification of the HSV-1 template DNA with pol primers resulted in the expected, pol PCR product (lane 2). The HSV-1 template DNA with ICP10 primers resulted in no product (lane 3). The HSV-2 DNA template with pol primers resulted in the pol product (lane 4). Thus, as expected, the pol primers did not discriminate between HSV-1 and HSV-2 and produced amplification products with both DNA templates. In contrast, the ICP10 promoter primers resulted in an amplification product with the HSV-2 DNA template only.

EXAMPLE 11

This example illustrates the cloning of the ICP10 promoter PCR product into the pGEM-T vector.

Figure 8:
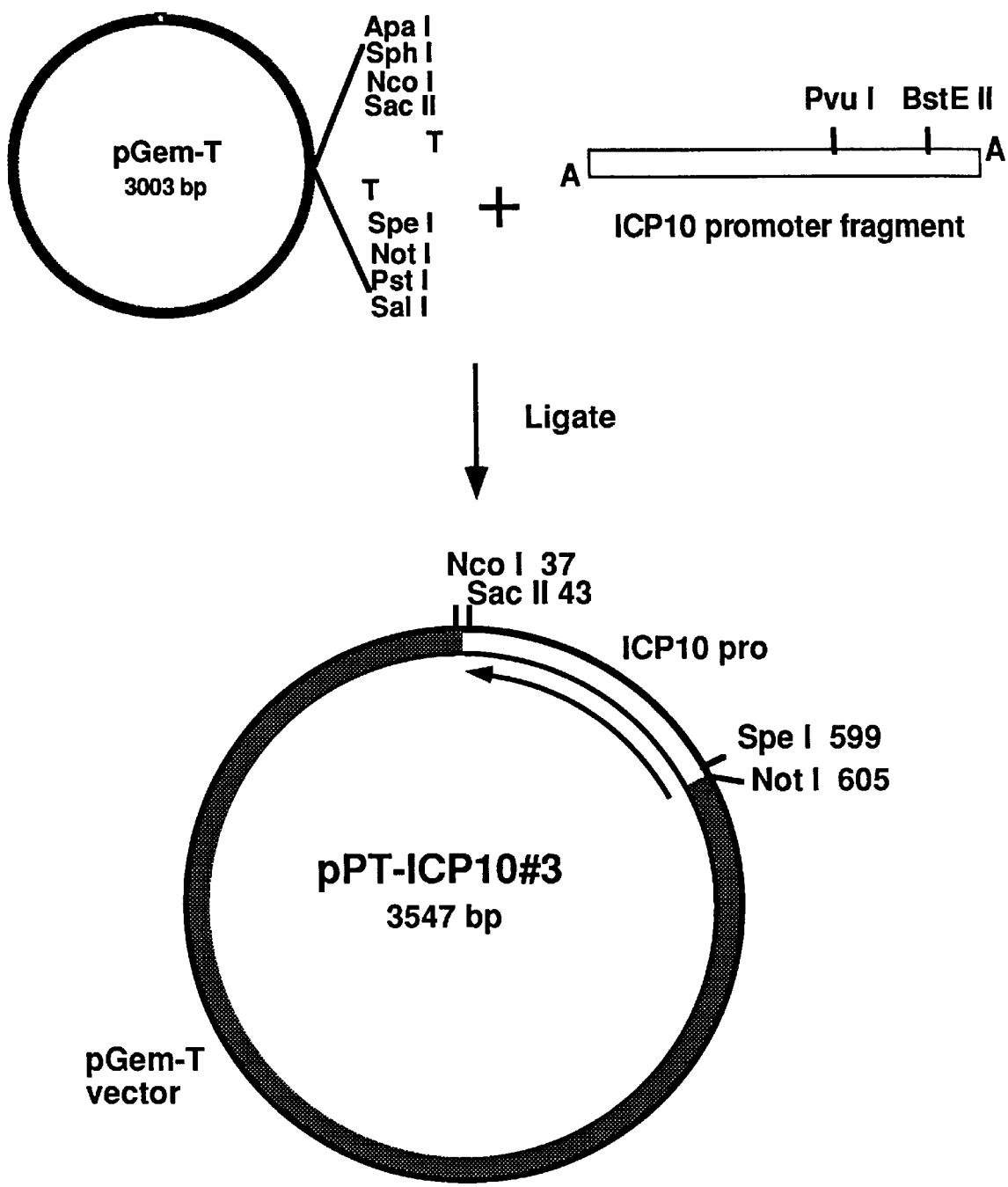
FIG. 8 is a schematic representation of the cloning of the ICP10 promoter PCR product into a pGEM-T vector.

The pGEM-T vector (obtained from Promega, Inc. Madison, Wis.) is a linear molecule with 3'-T overhangs to facilitate cloning of PCR products which have 3'-A ends added by the Taq polymerase. One microgram of pGEM-T was ligated to the ICP10 promoter PCR product which was purified on a low melting temperature agarose gel. The ligation mixture was then used to transform E. coli (DH5a strain). Plasmid DNA was harvested from bacterial colonies which grew on ampicillin plates. To determine whether the plasmid DNA from each colony contained the ICP10 promoter fragment, each plasmid sample was analyzed by restriction enzyme digestion and agarose electrophoresis. For initial screening plasmids were digested with Pst I. There are no Pst I cleavage sites in pGEM-T and no sites in the 543 bp ICP10 promoter fragment. PGEM-T is 3003 bp and pGEM-T plus the ICP10 fragment is 3547 bp in length. Samples with 3547 bp fragments were selected for further analysis. The samples were digested with Nco I (in pGEM-T) and BstE II (in the ICP10 promoter fragment) (see FIG. 8). Because PCR fragments can be ligated to pGEM-T in either orientation the predicted products of a double digestion with Nco I and BstE II would be either 109 bp and 3438 bp or 459 bp and 3088 bp. Plasmids consistent with both orientations were represented among the samples and one of each orientation was saved and designated pPT-ICP10#1 and pPT-ICP10#3.

EXAMPLE 12

This example illustrates cloning the E. coli lacZ gene immediately downstream of the ICP10 promoter.

The vector, pPT-ICP10#3, was digested with Not I. The DNA ends were converted to 'blunt' ends with Klenow and 4 dNTPs according to well established protocols. The pPT-ICP10#3 sample was then digested with Nco I. This resulted in release of a 568 bp fragment which contained the ICP10 promoter containing an ATG initiation codon at its 3' end. Another plasmid, pPOICP6LacZ was digested with Nco I and SnaB I. This resulted in two fragments: a 664 bp fragment and a 6028 bp fragment which contained both vector sequences and the lacZ gene with an Nco I site at its 5' end. The 6028 fragment and the 568 ICP10 promoter fragment were isolated and ligated together and the ligation reaction was used to transform E. coil. Ampicillin resistant colonies were isolated and plasmid DNA from ten colonies was harvested. The plasmids were then digested with Sac II which has one site in the ICP10 promoter and no sites in pPOICP6LacZ. All ten plasmids were linearized with Sac II resulting in a 6598 bp fragment consistent with the ICP10 promoter plasmid plus the 6028 lacZ containing vector. The plasmids were then digested with Sac II and Spe I which resulted in two fragments, a 6048 bp fragment and a 550 bp fragment, in all ten plasmid samples. This was consistent with the ICP10 promoter fragment being ligated to the lacZ gene. One plasmid sample was saved and designated pPTIC10LacZ. Further restriction enzyme digestions using Nco I, BstE II, and Pvu I were performed to verify that pPTIC10LacZ was as predicted.

Verification that the ICP10 promoter was operably linked to the lacZ gene was as follows: the vector pPTIC10LacZ was transfected into separate wells of BHK cells using lipofecin (Gibco/BRL) according to the manufacturer's suggestions. Forty-eight hours later the cells were superinfected with either HSV-1 or HSV-2, or mock infected. Sixteen hours later the cells were histochemically stained for β-galactosidase. Positive-stained cells were seen in both HSV-1 and HSV-2-infected wells but none were seen in the mock-infected wells.

This result was consistent with transactivation of the ICP10 promoter by HSV.

EXAMPLE 13

This example illustrates the preparation of a susceptible cell line genetically engineered to enable it to detect infectious Herpes Simplex Virus.

Figure 9:
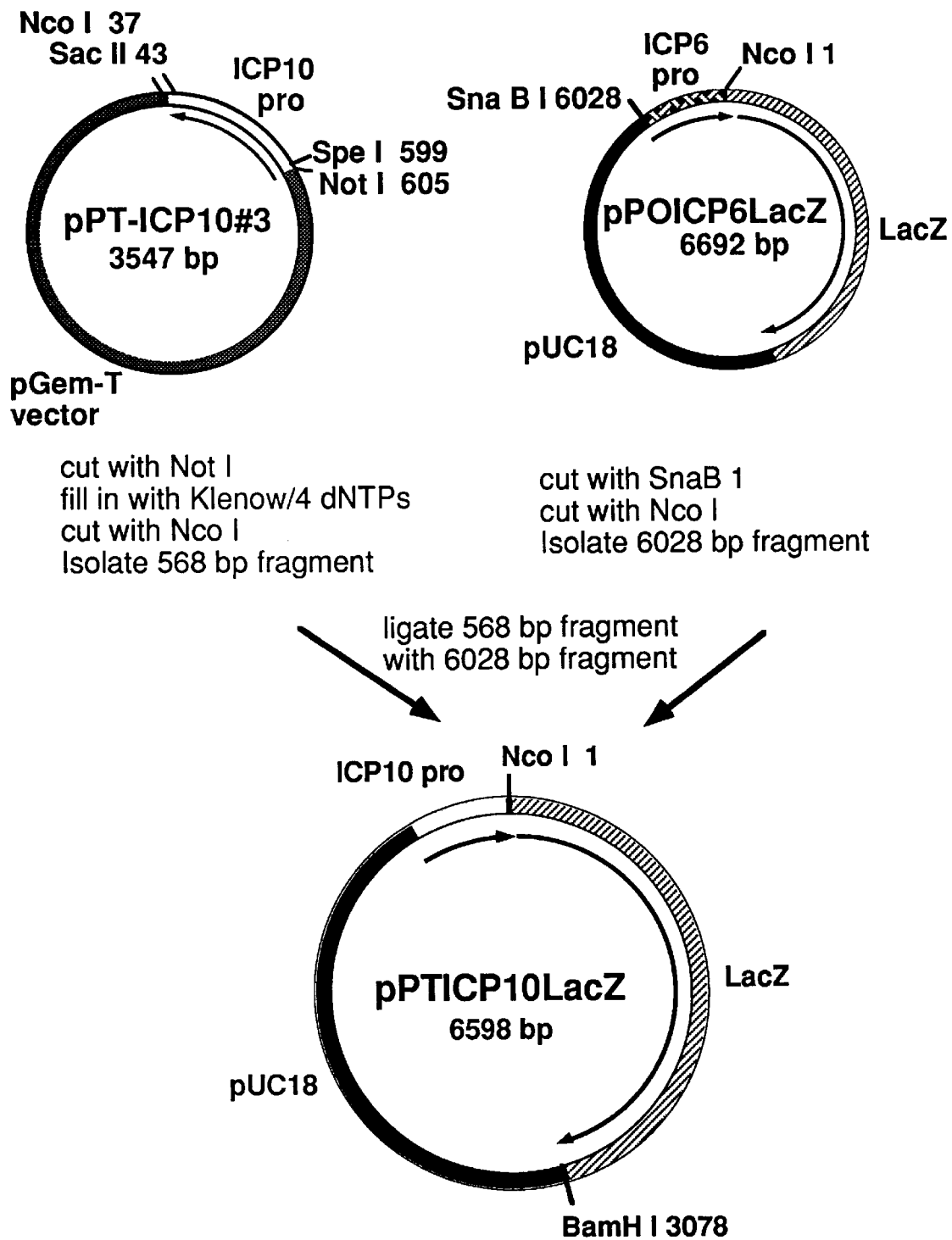
FIG. 9 is a schematic representation of the cloning of the E. coli LacZ gene immediately downstream of the ICP10 promoter.

Baby hamster kidney (BHK-21) cells were obtained from C. Hahn and C. Rice (Washington University, St. Louis, Mo.). The cells were propagated in MEM medium (Gibco-BRL, Gaithesburg, Md.) supplemented with 7% fetal calf serum (Gibco). Plasmid pPTC10LacZ containing HSV-2 ICP10 and lacZ were mixed with pMamNeo, which contains the neo gene in a 10 to 1 molar ration. These plasmids were then co-transfected into BHK-21 cells by the liposomal transfection protocol as described in Maniatis, T., et al. (Molecular Cloning: A Laboratory Manual, Cold Springs Harbor Laboratories, 1990 which is incorporated by reference) using reagents obtained from Gibco-BRL. The essential features of plasmid pPTIC10LacZ are shown in FIG. 9. The plasmid pPTIC10LacZ was prepared according to Example 12. Plasmid pMAMneo contains the SV40 early promoter-neomycin resistance gene cassette and was purchased commercially from Clontec, Palo Alto, Calif.

Twenty four hours after transfection, the cells were placed in selective medium containing 1 mg/ml G418 (Geneticin, Gibco: 50–60% active drug). The medium was changed daily for 4 days at which time the vast majority of the cells were killed. The cells were trypsinized and plated in 100 mm dishes in selective media. The media were changed every other day for one week and every four days thereafter. Following 1 to 2 weeks, the colonies that had formed were picked using a sterile trypsin/EDTA soaked cotton tip applicator and transferred to a 35 mm dish and grown in media containing 400 mg/ml G418. At least twenty separate clones were evaluated for HSV inducible β-gal activity. This initial screening was done by staining cell monolayers histochemically for β-gal activity following mock infection or infection with a laboratory strain of HSV-1 (KOS) or HSV-2 (strain 333). Those clones with high β-gal activity after infection were frozen for storage. One promising cell line, BHKICP10LacZ-17 (identified hereinafter as BHKICP10LacZ), displayed no detectable β-galactosidase activity after mock infection and pronounced activity following infection with HSV. This cell line was selected for further studies.

EXAMPLE 14

This example illustrates the ability of the BHKICP10LacZ to detect infectious herpes simplex virus in a specimen.

Cells from cell line BHKICP10LacZ as described in Example 12 were infected with HSV-1 OR HSV-2 at various multiplicities of infection (m.o.i.) in standard tissue culture medium. The cells and the virus were allowed to remain in culture for up to 12 hours after which the cells were assayed for β-galactosidase activity by the histochemical staining method in EXAMPLE 2.

Both HSV-1 and HSV-2 induced β-galactosidase activity that was demonstrable by 6 hours after infection. Control cells subject to no infection and mock infection exhibited no blue staining of the cells. Thus, the ICP10 promoter transfected into the cell line of this invention displays no constitutive expression and is transactivated on infection with HSV.

EXAMPLE 15

This example illustrates the specificity of BHKICP10LacZ cells in detecting only the presence of HSV in a specimen.

The specificity of the BHKICP10LacZ cells was determined according to the method in EXAMPLE 5. Monolayers of BHKICP10LacZ cells were inoculated, separately, with specimens known to contain other viruses and assayed histochemically for β-galactosidase activity. No β-galactosidase expression occurred 18 hours after infection of BHKICP10LacZ cells with each of four different viruses: varicella zoster virus, human cytomegalovirus, adenovirus type 5 and Sindbis virus. HSV-1 infection of BHKICP10LacZ cells resulted in β-galactosidase activity in a manner indistinguishable from HSV-2. Thus a cell line transfected with the ICP10 promoter and reporter gene as well as the method utilizing this cell line are specific for HSV-1 and HSV-2 (collectively HSV).

EXAMPLE 16

This example illustrates the stability of the transfected cell line BHKICP10LacZ.

The stability of BHKICP10LacZ cells was demonstrated by six passages in the absence of G418 selective pressure after which time the β-galactosidase activity was still inducible by HSV.

Genotypic analysis using PCR techniques confirmed the identity and stability of the BHKICP10LacZ cell line. Total cellular DNA was extracted from BHKICP10LacZ cells passed in the absence of selective pressure (i.e. without G418) and also from parental BHK cells. Using 5' primers homologous to the HSV-2 ICP10 promoter and 3' primers homologous to the lacZ open reading frame, a 500 bp fragment was amplified from the BHKICP10LacZ cells but not from the BHK cells. This demonstrated that the ICP10 promoter and the lacZ gene remained contiguous and that the BHKICP10LacZ cells are stably transformed with the ICP10 promoter:lacZ chimeric gene.

EXAMPLE 17

This example illustrates the preparation of susceptible cell lines transformed with a UL45 promoter/reporter gene construct which can detect infectious Human Cytomegalovirus.

Figure 11A:
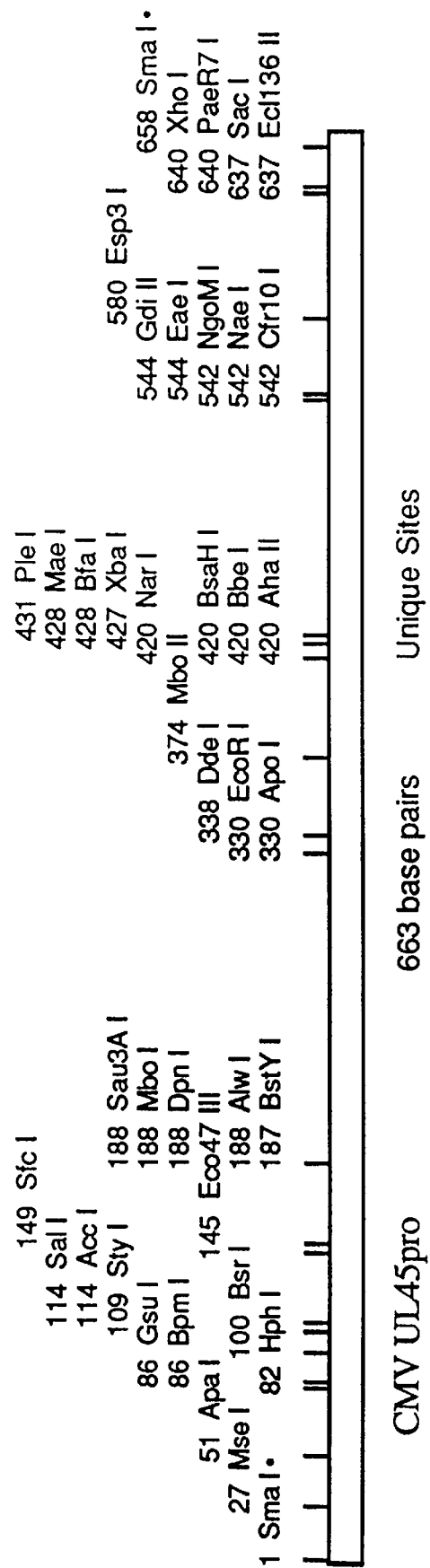
FIG. 11 illustrates (A) a detailed restriction map of a 663 bp region of the HCMV UL45 gene which contains the promoter and part of the open reading frame (ORF) and (B) the DNA sequence of this region (SEQ ID NO:3).
Figure 12:
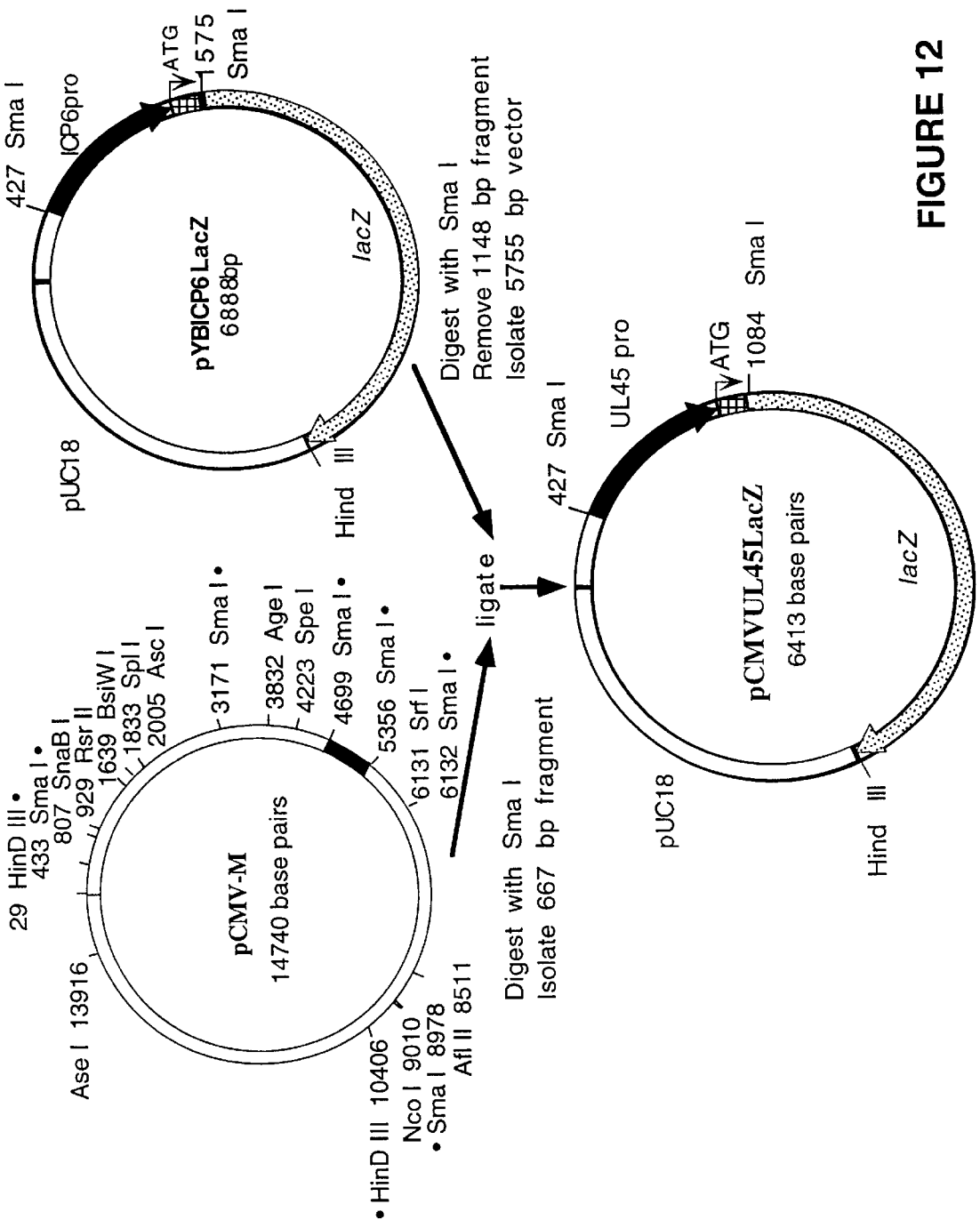
FIG. 12 is a schematic representation of the construction of a recombinant plasmid, pCMVUL45LacZ, containing a chimeric UL45 promoter:lacZ gene.

The promoter for the UL45 gene, which is the HCMV homolog of the HSV UL39 gene, was isolated and cloned using the publically available HCMV genomic sequence (GenBank Accession No. X17403) and standard molecular biology techniques. In brief, analysis of the known HCMV sequence placed the UL45 gene within a 10,383 base pair HindIII fragment which was isolated from a complete HindIII digestion of HCMV genomic DNA by gel electrophoresis. (FIG. 10A.) The isolated HindIII fragment containing the UL45 gene was then cloned into the HindIII site of pBR322 to generate pCMV-M (FIG. 10B). Based on the known HCMV sequence, a 663 base pair region bounded by SmaI sites of pCMV-M (FIG. 11A) was identified which contained 177 base pairs of the UL45 open reading aframe (ORF) and 483 base pairs of upstream sequence containing the UL45 promoter. (FIG. 11B, SEQ ID NO:3). As illustrated in FIG. 12, this region was cloned by digesting PCMV-M with SmaI and inserting the resulting 657 bp SmaI fragment into SmaI-digested pYBICP6LacZ, thereby replacing the HSV UL39 promoter with the HCVM UL45 promoter to generate pCMVUL45LacZ (FIG. 12). Restriction digestion confirmed that the UL45 promoter/partial ORF were in the same orientation as the LacZ ORF. The predicted product of the chimeric UL45 promoter-LacZ gene in pCMVUL45LacZ is a fusion protein containing 59 amino acids of the UL45 protein fused to the amino terminus of β-galactosidase (FIG. 13, SEQ ID NO.4).

Vero cells (african green monkey kidney cells) and MRC-5 cells were transiently transfected with pCMVUL45LacZ and subjected to a mock infection or to infection with HCMV. A histochemical assay using X-Gal as the substrate for β-galactosidase showed no staining of mock-infected cells and blue staining of the HCMV-infected cells (data not shown). This experiment demonstrated that the UL45 promoter in transiently transfected Vero or MRC-5 cells was nonconstitutive in the absence of HCMV and yet inducible upon HCMV infection.

Vero cells were also stably transformed with the UL45:LacZ chimeric gene and infected with HCMV at a m.o.i. of 10. Expression of immediate early (IE) antigen was detected in 10% of the stably transformed infected cells and an equal number of cells stained positive for β-galactosidase in a histochemical assay (data not shown). Thus, Vero cells stably transformed with the UL45 promoter are capable of detecting infectious HCMV even though Vero cells have a low susceptibility to infection with HCMV compared with primary human cells such as MRC5 cells.

Figure 14:
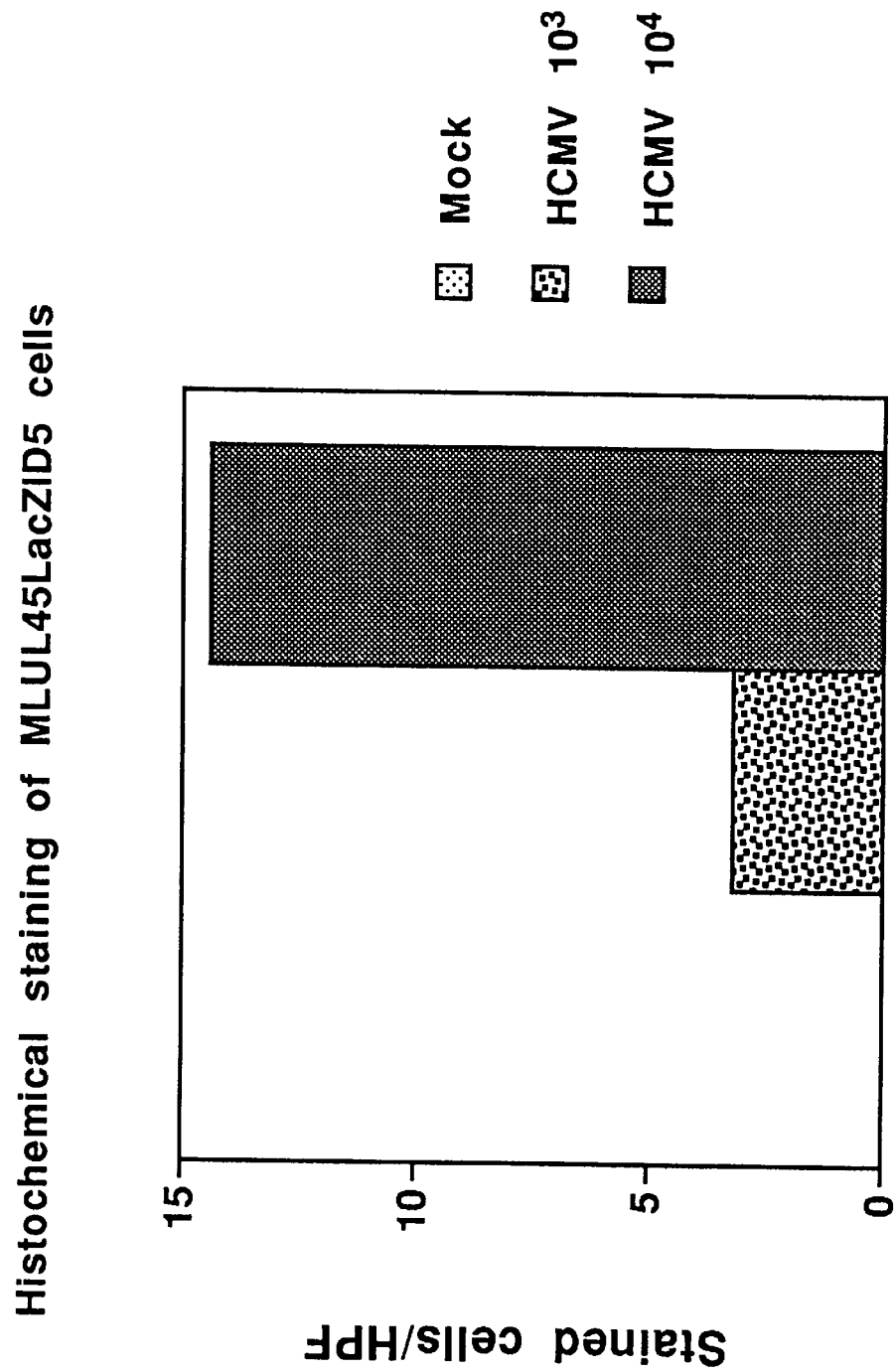
FIG. 14 is a graphical representation of β-galactosidase activity in HCMV-infected mink lung cells stably transformed with the chimeric UL45 promoter:LacZ gene (MLUL45LacZID5 cells) as measured by a histochemical staining assay.

Because mink lung (ML) cells have been used by clinical laboratories to detect HCMV using an immunofluoresence assay (Gleaves et al., *J. Clin. Microb.*, 30:1045–1048, 1992, incorporated herein by reference), a mink lung cell line (ATCC CCL 64) was stably transformed with pCMVUL45LacZ using hygromycin resistance as a selectable marker. A clone containing the UL45:LacZ chimeric gene was identified and designated MLUL45LacZ-ID5. To test this cell line for the ability to detect HCMV, $5 \times 10^5$ MLUL45LacZ-ID5 cells were plated in each well of a 24 well plate, incubated overnight at 37° C., and then inoculated with $10^3$ or $10^4$ plaque-forming units of HCMV (Towne strain) per well or mock-infected. After incubation for 48 hours at 37° C., the cells were fixed and histochemically stained for β-galactosidase activity as described in Example 2. The mean of blue cells observed in 20 high power fields (200× magnification) was determined and the results shown in FIG. 14. A significant number of cells from the HCMV-infected MLUL45LacZ-ID5 cultures stained positive for β-galactosidase whereas no blue cells were detected in mock-infected cultures, indicating that the UL45 promoter in the MLUL45LacZ-ID5 cell line is nonconstitutive and HCMV-inducible.

EXAMPLE 18

This example illustrates detection of HCMV with the MLUL45LacZ-ID5 cell line using a rapid calorimetric assay.

Cultures containing $5\times10^4$ of parental or stably transformed mink lung cells were mock-infected or infected with $8\times10^4$ pfu of HCMV (m.o.i. of about 1.6). At 48 hrs post infection, cells were removed from the cultures, lysed and assayed for the amount of β-galactosidase activity with a colorimetric assay using the substrate CPRG and 3 or 15 hrs of color development.

Figure 15A:
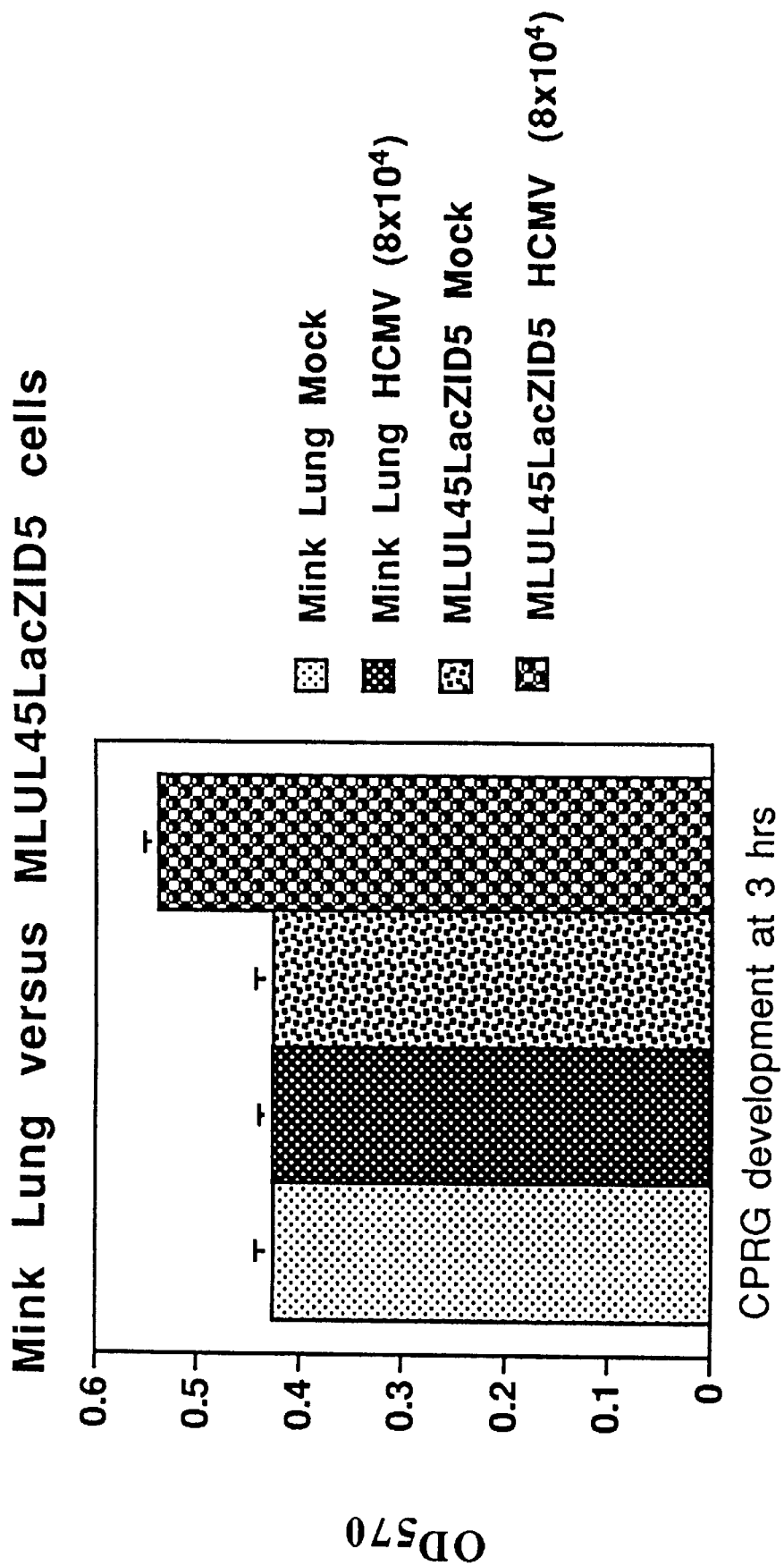
FIG. 15 is a graphical representation of β-galactosidase activity in parental Mink Lung cells and MLUL45LacZID5 cells that have been mock-infected or infected with HCMV for 48 hours as measured by a calorimetric assay on cell lysates using a 3 hour (A) or 15 hour (B) substrate incubation time.
Figure 15B:
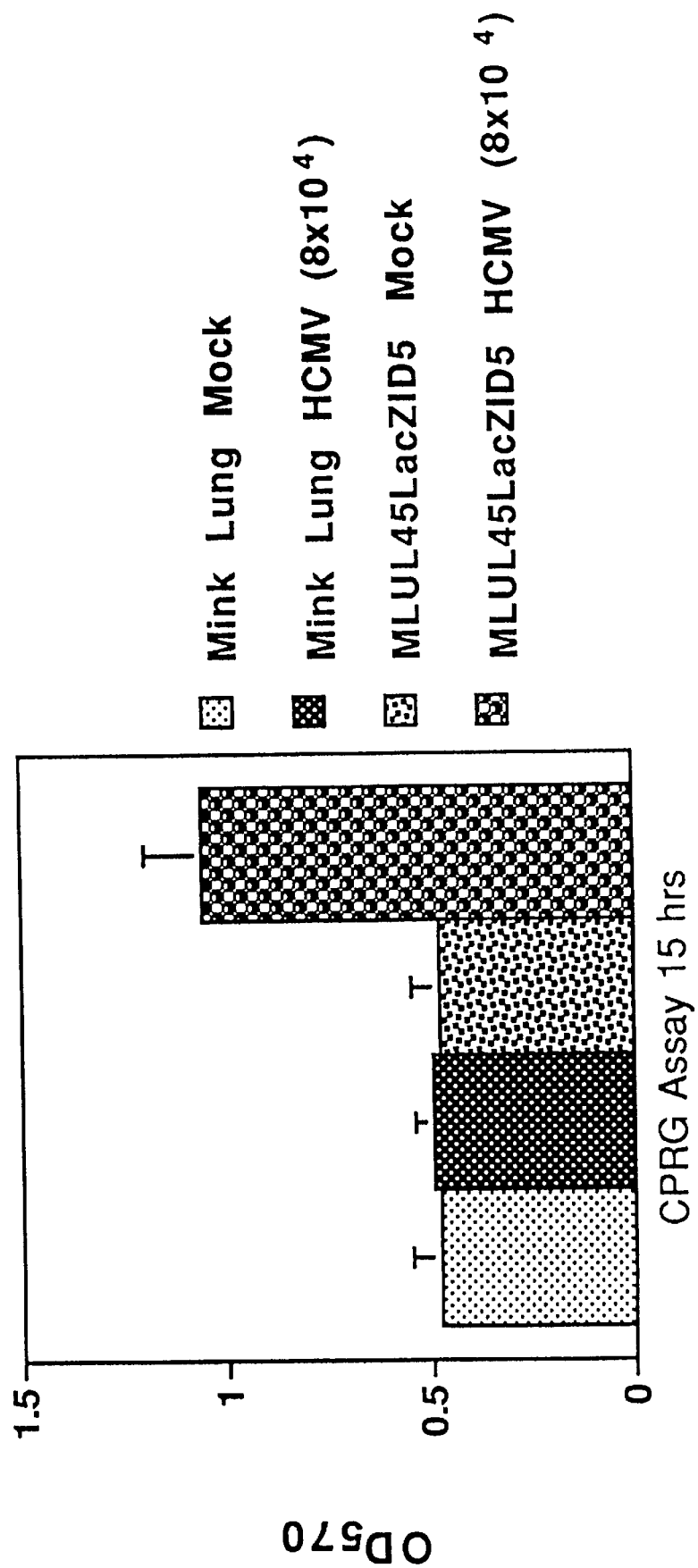

As shown in FIG. 15, there was no significant difference in the amount of CPRG hydrolysis, as measured at $OD_{570}$, in lysates from the controls, i.e., mock-infected or HCMV-infected parental mink lung cells and mock-infected MLUL45LacZ-ID5 cells, whether incubated with substrate for 3 hrs (FIG. 15A) or 15 hrs (FIG. 15B). Thus, any reporter gene expression induced by the UL45 promoter in the absence of HCMV is nonconstitutive, i.e., not detectable above the background amount of substrate hydrolysis measured in the mock-infected or HCMV-infected controls. However, in the presence of HCMV, a significant increase in enzyme activity over background was observed in MLUL45LacZ-ID5 cells (FIG. 15A), and an even greater difference was observed when activity was measured after a 15 hr incubation. Thus, the presence of HCMV is readily detectable by the MLUL45LacZ-ID5 cells.

EXAMPLE 19

This example illustrates that the detection sensitivity of the MLUL45LacZ-ID5 cell line is increased with sodium butyrate (NaB).

MLUL45LacZID5 cells ($5\times10^4$) were incubated in the presence or absence of 80 mM NaB for 24 hrs prior to infection. Just before inoculation of the cultures with virus, the culture media was removed, the cells were washed, and fresh media containing 8 mM NaB was added. The cells were then infected with $3.2\times10^2$ or $2.5\times10^3$ pfu of HCMV (m.o.i. of 0.0064 or 0.05) and incubated in the presence of the 8 mM NaB for 48 hrs. Aliquots of the cultures were lysed and the lysates analyzed for β-galactosidase activity using CPRG as the substrate in a colorimetric assay. The results are shown in FIG. 16.

Figure 16:
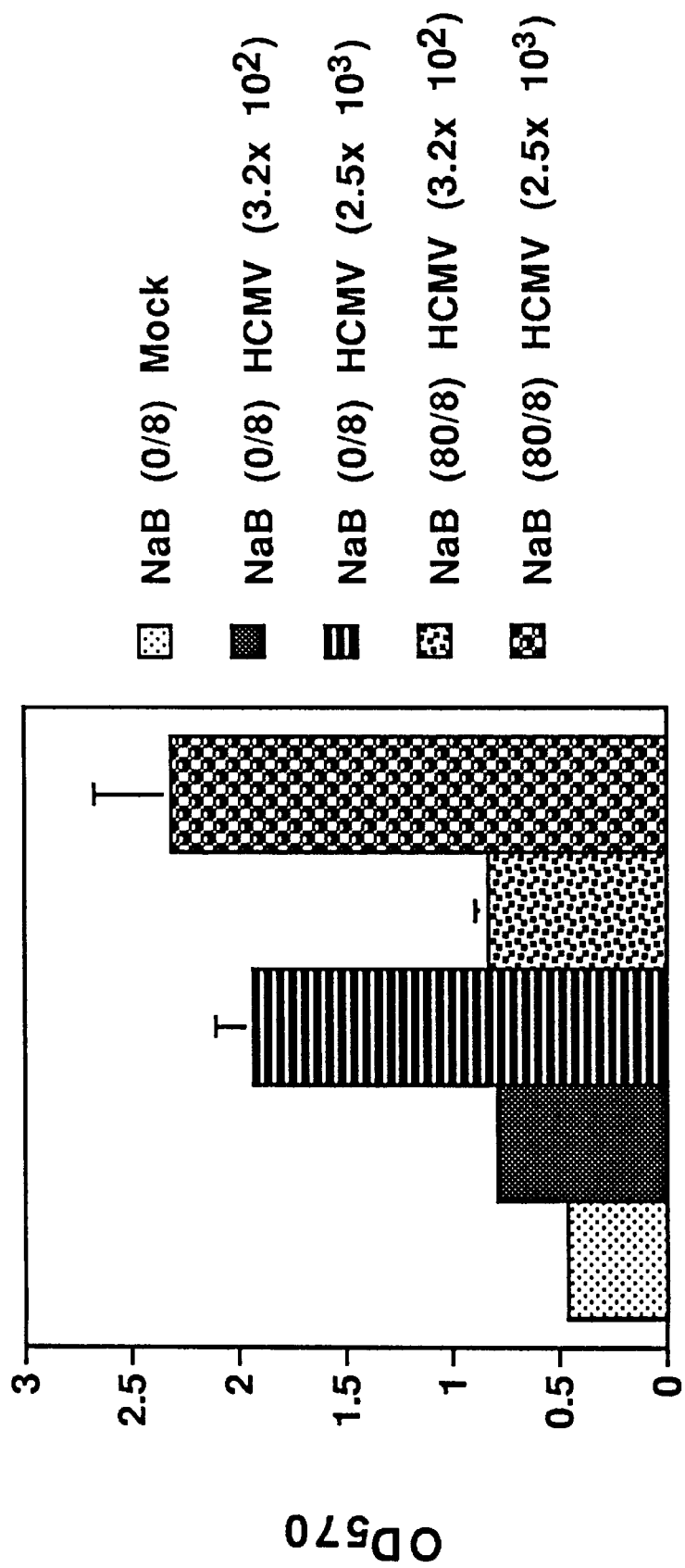
FIG. 16 is a graphical representation of β-galactosidase activity in MLUL45LacZID5 cells incubated with sodium butyrate (NaB) both before and after infection or only after infection as measured by a colorimetric assay on cell lysates.

In mock-infected cells treated with NaB post infection (0/8), the background $OD_{570}$ was similar to that seen in parental mink lung cells not treated with NaB (compare FIG. 15B with FIG. 16). In HCMV-infected MLUL45LacZID5 cells that were treated with NaB, an increase in β-galactosidase activity was detected that was directly related to the amount of infecting virus. The amount of activity detected in the NaB-treated infected cells was significantly higher at a 10- to 100-fold lower m.o.i. than that in the nontreated cells. Further, this NaB-induced increase in β-galactosidase activity was similar whether the cells were treated with NaB both before and after infection (80/8) or only treated with NaB after infection (0/8). Thus, induction of enzyme activity in the MLUL45LacZID5 cells by HCMV infection can be significantly increased by incubating the infected cells with sodium butyrate.

Although Examples 17–19 illustrate detection of HCMV with stably transformed mink lung cells, other susceptible cell lines known in the art can be used. In particular, a baby hamster kidney cell line stably transformed with the UL45-LacZ chimeric gene shows β-galactosidase activity after infection with HCMV as measured by histochemistry using the β-galactosidase substrate X-gal or by a calorimetric assay of cell lysates using CPRG as the substrate (data not shown). As in the MLUL45LacZ-ID5 cell line, the HCMV-induced β-galactosidase activity in these stably transformed baby hamster kidney cells is significantly increased when treated with sodium butyrate treatment as described above.

EXAMPLE 20

Figure 17A:
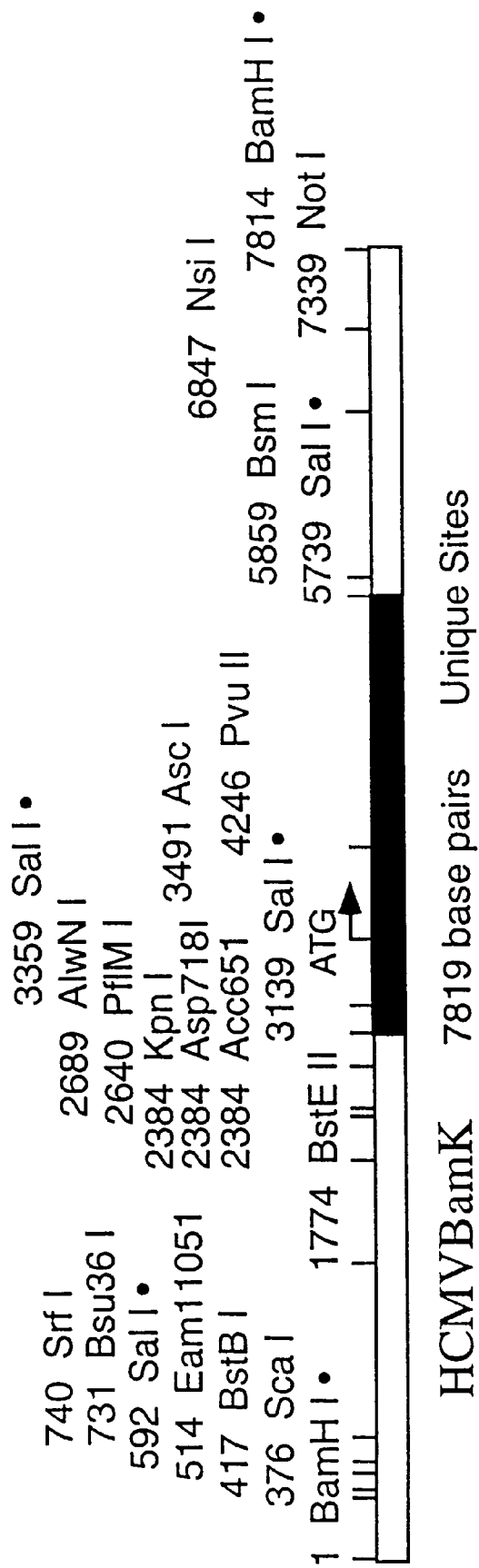
FIG. 17 illustrates (A) a restriction map of an HCMV genomic BamHI K fragment containing the UL57 gene and (B) a recombinant plasmid, pCMV-BK, generated by cloning this HCMV genomic BamHI K fragment into pBR322.
Figure 17B:
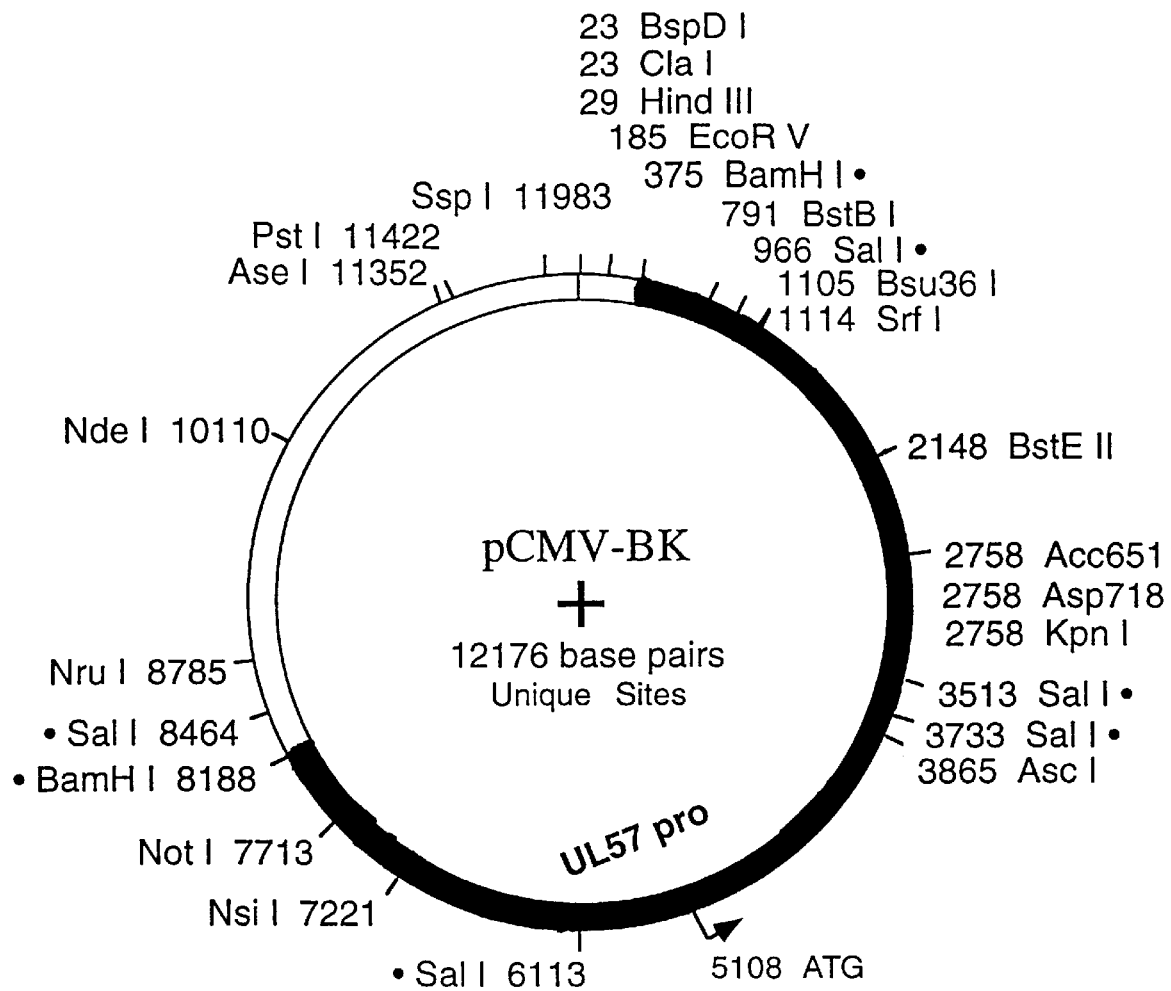
Figure 18A:
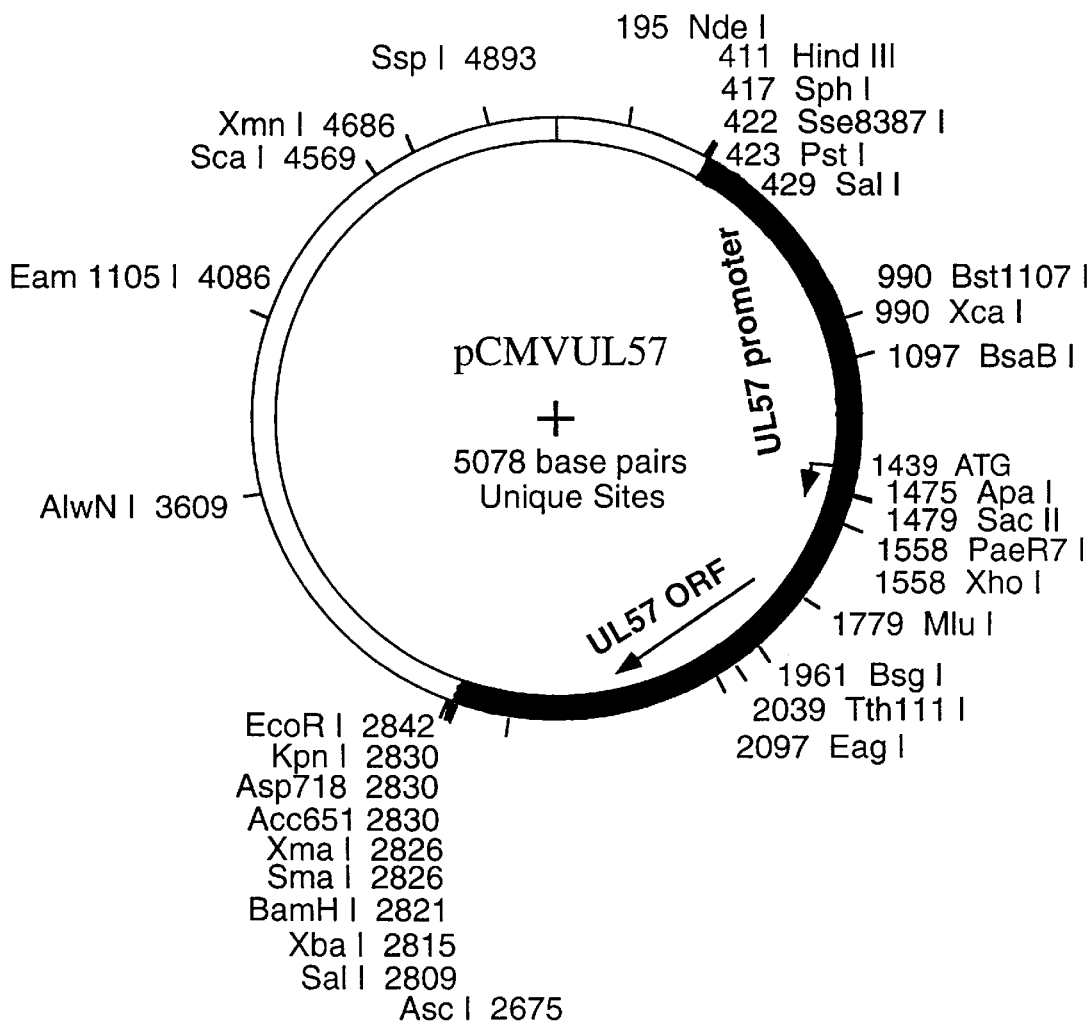
FIG. 18 is a schematic representation of (A) pCMVUL57 containing the promoter and a 51 portion of the ORF of the HCMV UL57 gene and (B) pCMVUL45LacZ generated by cloning the LacZ gene immediately downstream of the partial UL57 ORF in pCMVUL57.
Figure 18B:
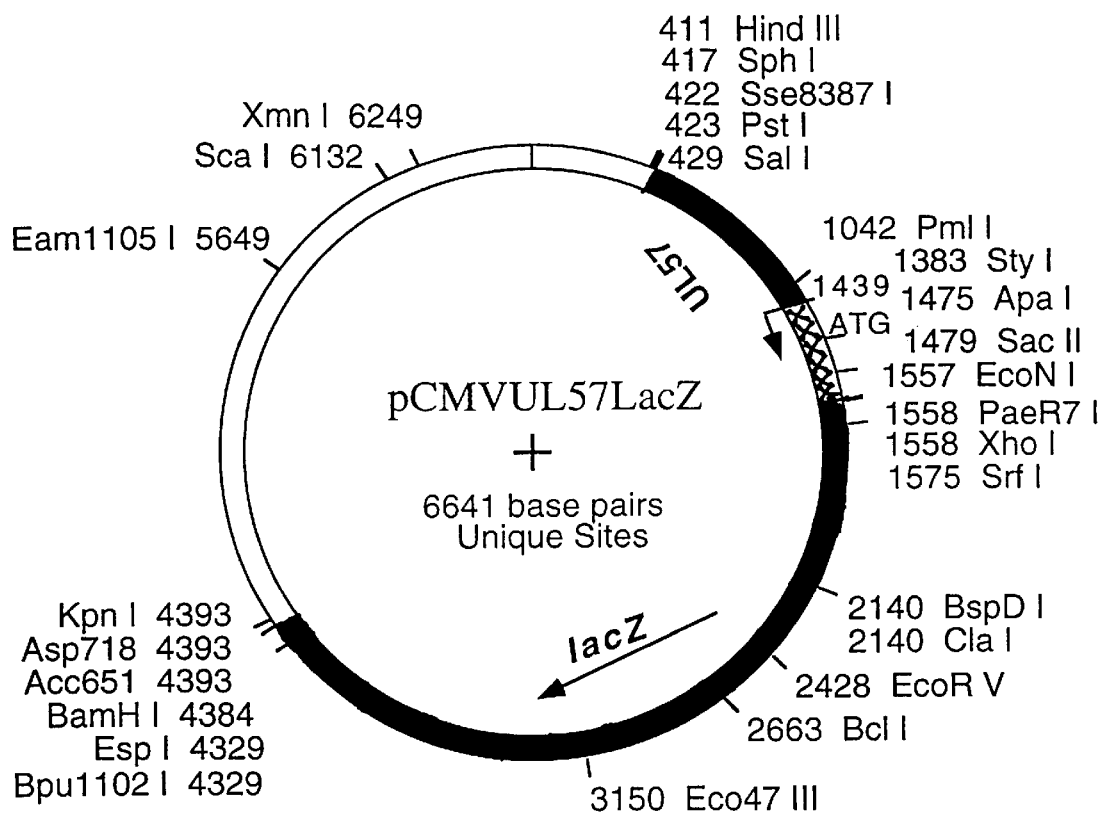

This example illustrates that another beta promoter, the UL57 gene promoter of HCMV, is induced by HCMV in a cell line transiently transfected with a plasmid containing a UL57 promoter-LacZ construct The UL57 gene, which is the homolog of the HSV-1 UL29 gene, was determined by computer analysis of the known HCMV genomic sequence to reside in a 7819 bp region bounded by BamHI sites (FIG. 17A). This region was isolated by digestion of HCMV genomic DNA with BamHI and the resulting BamHI K fragment was cloned into pBR322 to generate pCMV-BK (FIG. 17B). A 2380 bp SalI fragment containing the UL57 promoter and a 5' portion of the UL57 ORF was isolated from pCMV-BK and cloned into the SalI site of the vector pUC18 to generate pCMVUL57 (FIG. 18A). Double digestion of pCMVU157 with XhoI and BamHI produced a 1263 bp XhoI/BamHI fragment which was replaced by a 2826 bp XhoI/BamHI fragment from pCMVUL45LacZ which contains the LacZ ORF. The resulting plasmid, pCMVUL57LacZ (FIG. 18B), contains the UL57 promoter immediately upstream of an in-frame fusion of the first 40 codons of UL57 with the LacZ ORF.

Figure 19:
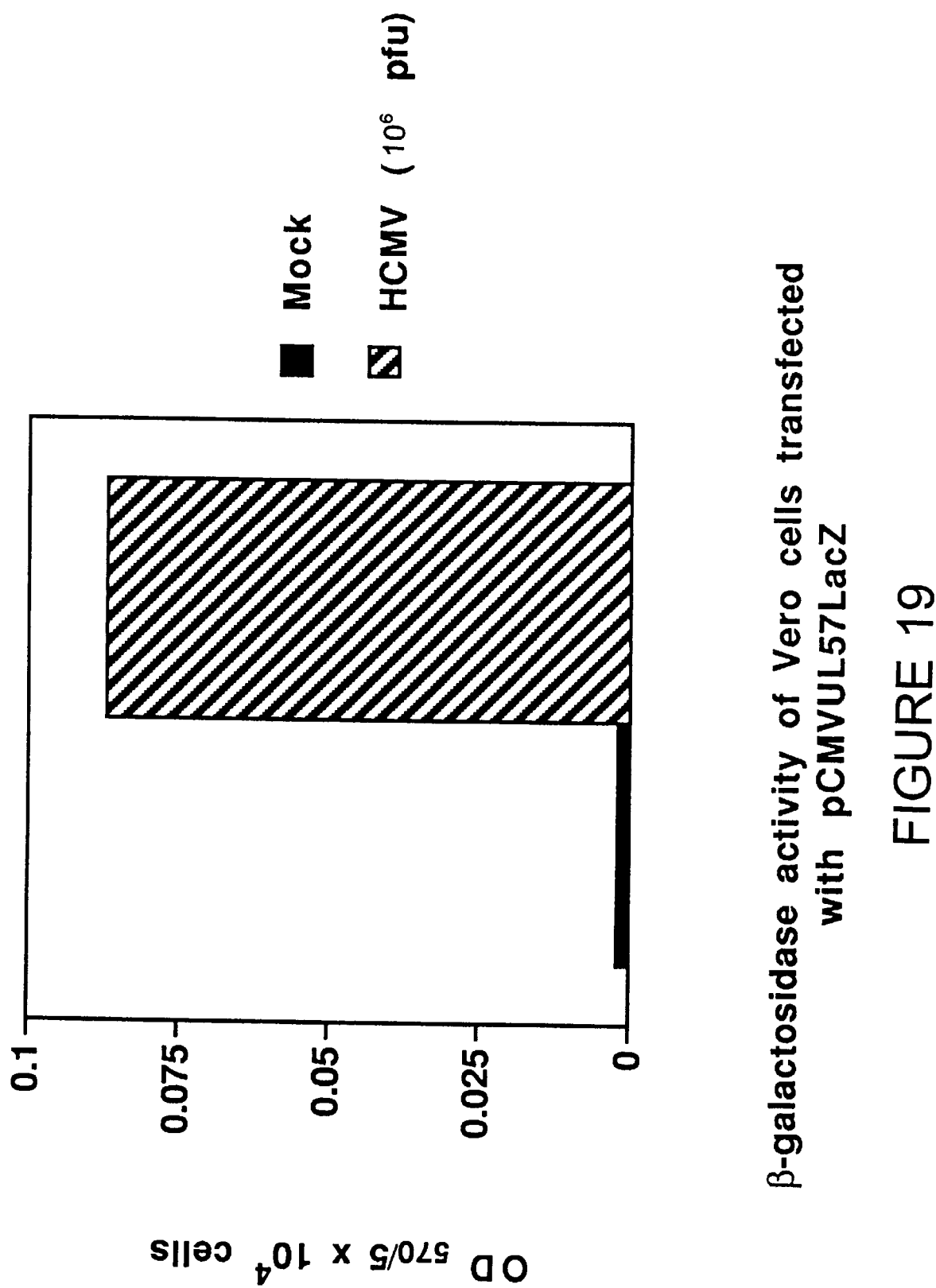
FIG. 19 is a graphical representation of β-galactosidase activity in mock-infected and HCMV-infected Vero cells transiently transfected with pCMVUL57LacZ showing that the UL57 promoter is inducible by infection with HCMV as measured by a calorimetric assay on cell lysates.

To determine if the UL57 promoter is inducible by HCMV, $5\times10^5$ Vero cells were plated in the wells of a 6-well dish, incubated overnight at 37° C., and transiently transfected with 0.5 micrograms of pCMVUL57LacZ or a control plasmid (pUC18) using lipofectamine. The transiently transfected cells were cultured for 24 hrs at 37° C. and then mock-infected or infected with HCMV ($10^6$ pfu) and incubated for an additional 24 hrs. The cells were lysed and an aliquot was assayed for β-galactosidase activity using CPRG as the substrate in a colorimetric assay. As shown in FIG. 19, the amount of hydrolyzed substrate as measured by $OD_{570}$ per $5\times10^4$ cells was more than 40-fold greater in the HCMV-infected cells than in the mock-infected cells. Thus, the UL57 promoter in these transiently transfected cells is induced in the presence of HCMV.

In view of the above, it will be seen that the several objects of the invention are achieved and other advantageous results attained.

As various changes could be made in the above constructions without departing from the scope of the invention, it is intended that all matter contained in the above description shall be interpreted as illustrative and not in a limiting sense.

What is claimed is:

1. An in vitro diagnostic method to detect infectious Human Cytomegalovirus in a specimen, said method comprising the steps of:

providing a genetically engineered cell line stably transformed with a sequence of DNA containing a beta-gene promoter sequence of Human Cytomegalovirus, wherein said promoter sequence is operably linked to a reporter gene, the expression of the reporter gene being non-constitutive and dependent upon the presence of Human Cytomegalovirus;

inoculating the cell line with a specimen suspected of containing Human Cytomegalovirus;

allowing a period of time for the infectious cycle of Human Cytomegalovirus to proceed; and detecting the infectious Human Cytomegalovirus in said specimen.

2. The method of claim 1 wherein said promoter sequence contains a promoter for a gene that encodes a ribonucleotide reductase or a subunit of a ribonucleotide reductase.

3. The method of claim 2 wherein said promoter sequence contains a UL45 promoter.

4. The method of claim 1 wherein said reporter gene encodes an enzyme capable of being detected by a calorimetric, fluorimetric or luminometric assay.

5. The method of claim 4 wherein said enzyme is a β-galactosidase.

6. The method of claim 5 wherein said detection step involves detecting an activity of the β-galactosidase by histochemical/light microscopy.

7. The method of claim 5 wherein said detection step involves detecting an activity of the β-galactosidase on a fluorogenic substrate.

8. The method of claim 1 wherein said genetically engineered cell line is from a mink lung cell line.

9. The method of claim 8 wherein said promoter sequence contains a UL45 promoter and said reporter gene encodes a β-galactosidase.

10. A genetically engineered cell line stably transformed with a sequence of DNA containing a beta-gene promoter sequence from Human Cytomegalovirus wherein said promoter sequence is operably linked to a reporter gene, the expression of the reporter gene being nonconstitutive and dependent upon the presence of Human Cytomegalovirus.

11. The cell line of claim 10 wherein said promoter sequence contains a promoter for a gene that encodes a ribonucleotide reductase or a subunit of a ribonucleotide reductase.

12. The cell line of claim 11 wherein said promoter sequence contains a UL45 promoter.

13. The cell line of claim 10 wherein said reporter gene encodes an enzyme capable of being detected by a calorimetric, fluorimetric or luminometric assay.

14. The cell line of claim 13 wherein said enzyme is a β-galactosidase.

15. The cell line of claim 10 wherein said genetically engineered cell line is from a mink lung cell line.

16. The cell line of claim 15 wherein said promoter sequence contains a UL45 promoter and said reporter gene encodes a β-galactosidase.

17. A kit for assaying for the presence of infectious Human Cytomegalovirus in a specimen, said kit comprising:
a supply of a genetically engineered mammalian cell line susceptible to infection by Human Cytomegalovirus, the cell line comprising a stably transformed sequence of DNA containing a beta-promoter sequence of Human Cytomegalovirus operably linked to a reporter gene, the expression of said reporter gene being nonconstitutive and dependent upon the presence of Human Cytomegalovirus in the specimen; and a supply of reagents to detect the expression of said reporter gene.

18. The kit of claim 17 wherein said promoter sequence contains a promoter for a gene that encodes a ribonucleotide reductase or a subunit of a ribonucleotide reductase.

19. The kit of claim 18 wherein said promoter sequence contains a UL45 promoter.

20. The kit of claim 17 wherein said reporter gene encodes an enzyme capable of being detected by a calorimetric, fluorimetric or luminometric assay.

21. The kit of claim 20 wherein said enzyme is a β-galactosidase.

22. The kit of claim 21 wherein said reagents include a 5-bromo-4-chloro-3-indolyl-β-D-galactopyranoside solution.

23. The kit of claim 17 wherein the genetically engineered cell line is from a mink lung cell line.

24. The kit of claim 23 wherein said promoter sequence contains a UL45 promoter and said reporter gene encodes a β-galactosidase.

* * * * *